United States Patent [19]
Tondeur et al.

[11] Patent Number: 5,916,985
[45] Date of Patent: Jun. 29, 1999

[54] FUNCTIONALISED POLYMERS, METHOD FOR SYNTHESISING SAME AND USE THEREOF AS SURFACTANTS, PARTICULARLY IN COSMETIC COMPOSITIONS SUCH AS NAIL VARNISH

[75] Inventors: Carole Tondeur, Mulhouse; Catherine Garel, Riedisheim; Henri-Gérard Riess, Mulhouse; Alain Meybeck, Courbevote; Jean-Francois Tranchant, Boigny-sur-Bionne, all of France

[73] Assignee: LVMH Recherche, France

[21] Appl. No.: 08/817,387

[22] PCT Filed: Sep. 28, 1995

[86] PCT No.: PCT/FR95/01251

§ 371 Date: Mar. 28, 1997

§ 102(e) Date: Mar. 28, 1997

[87] PCT Pub. No.: WO96/10043

PCT Pub. Date: Apr. 4, 1996

[30] Foreign Application Priority Data

Sep. 28, 1994 [FR] France ................... 94 11575

[51] Int. Cl.$^6$ ....................................... C08F 2/00
[52] U.S. Cl. ......................... 526/214; 526/329.7
[58] Field of Search .................. 526/214, 329.7

[56] References Cited

U.S. PATENT DOCUMENTS

| | | |
|---|---|---|
| 3,684,771 | 8/1972 | Braun . |
| 3,689,593 | 9/1972 | Jackson . |
| 3,788,996 | 1/1974 | Thompson . |
| 4,032,698 | 6/1977 | Ashe . |
| 4,070,388 | 1/1978 | Jones . |
| 5,091,573 | 2/1992 | Gross et al. . |
| 5,298,585 | 3/1994 | McCallum, III et al. . |

OTHER PUBLICATIONS

E. Goethals, "Telechelic Polymers Synthesis and Applications", CRC Press (1989), 169–179.
Y. Yamashita et al. "Syntheses of Polyamide–Poly(methyl Methacrylate Graft Copolymers by Polycondensation Reactions of Macromonomers" Polymer Bulletin, 5, (1981), 361–366.
Y. Chujo et al., "Synthesis of Aromatic Dicarboxyl–Terminated Poly(methyl Methacrylate) Macromonomers", Journal of Polymer Science: Part A: Polymer Chemistry, vol. 27 2007–2014 (1989).
H. Jakubauskas, "Use of A–B Block Polymers as Dispersants for Non–Aqueous Coating Systems", J. Coat. Techn. 58, No. 736 (1986), pp. 71–82.

H. Baumann, B. Joos, W. Funke, "Emulsifying Properties of Saturated Polyesters"—Makromol. Chem., 187, 2933 (1986).
H. Baumann, B. Joos, W. Funke, "Saturated Polyesters as Emulsifiers for Emulsion Copoly merization of Unsaturatd Polyester Resins with Styrene"—Makromol. Chem. 190, 83–92 (1989).
M. Miyata, W. Funke, "Reactor Microgels by Self–Emulsifying Copolymerization of Unsturated Polyester Resins with Acrylic and Methacrylic Esters"—Makromol. Chem. 184, 755–762 (1983).
Y.–Ch. Yu, W. Funke, "Reactive Microgels by Emulsion Polymerization of Unsaturated Polyester Resins"—Die Angewandte Makromol. Chem. 103, 187–202 (1982).
Y.–Ch. Yu, W. Funke, "Surfactant Properties of Unsaturated Polyesters"—Die Angewandte Makromol. Chem. 103, 203–215 (1982).
P. Stevens et al. "Wetability of Powders",*Farmaceutish Tijdschrift voor Belgie,* 51 ejaargang, No. 2, maat, Apr. 1974.

*Primary Examiner*—Bernard Lipman
*Assistant Examiner*—N. Sarofin
*Attorney, Agent, or Firm*—Bierman, Muserlian and Lucas

[57] ABSTRACT

The invention relates to a functionalised polymer of formula:

$$(P)-S-X-F \tag{1}$$

in which:
- (P) is a hydrophobic polymer chain obtained by radical polymerisation of at least one monomer,
- S represents sulphur,
- X represents:
  - a saturated or unsaturated linear or branched hydrocarbon chain having 1 to 6 carbon atoms and substituted with at least one COOH or $NH_2$ group in the free or salified form
  - a peptide chain constituted of 2 to 4 amino acids, particularly natural amino acids,
- F represents a COOH or $NH_2$ group, in the free or salified form, with the exception of the ω-dicarboxylic macromonomers resulting from the radical polymerisation of a monomer in the presence of a chain transfer agent constituted of thiomalic acid. The invention also relates to the use of the above functionalised polymers as well as to those resulting from the radical polymerisation of a monomer in the presence of thiomalic acid, as surfactant especially as wetting agent, dispersing agent, stabilising agent of dispersion of particles or for preparing microdispersions. The invention also relates to cosmetic compositions including these polymers and especially nail varnishes.

42 Claims, 8 Drawing Sheets

FUNCTIONALISED POLYMERS, METHOD FOR SYNTHESISING SAME AND USE THEREOF AS SURFACTANTS, PARTICULARLY IN COSMETIC COMPOSITIONS SUCH AS NAIL VARNISH

The present invention relates to novel functionalised polymers, method for synthesising same and uses thereof as surfactants, especially as wetting agents and/or dispersing agents and/or stabilising agents of dispersions of solid particles, and for preparing microdispersions.

Chain end-functionalised polymers are already known and, more particularly, functionalised polymers obtained by polymerisation in the presence of a chain transfer agent constituted of a thiol.

More particularly, work in this field by Y. YAMASHITA, Y. CHUJO et al. will be cited. The authors have essentially described the synthesis of methyl polymethacrylates (PMMA) having —OH or —COOH end groups, together with their use in the preparation of macromonomers and as macromonomers for polycondensations. These pieces of work are stated in "Telechelic Polymers Synthesis and Applications" E. J. GOETHALS, CRC Press Inc. (1989) 169–179.

Macromonomers of general formula (PMMA) SCH (COOH)CH$_2$COOH, as well as other acrylic macromonomers having the same end function, are described by Y. YAMASHITA, Y. CHUJO, H. KOBAYASHI and KAWAKAMI in Polym. Bull., 5, 361–366 (1981). All these macromonomers are intended for use in polycondensation operations.

Macromonomers which are also intended for polycondensation operations are described by Y. CHUJO, H. KOBAYASHI and Y. YAMASHITA in J. of Polym. Sci., Part A: Polym. Chem., 27, 2007–2014 (1989), these macromonomers being constituted of a polymer PMMA chain with a dicarboxylic aromatic functional end group.

In all these documents, the functionalised macromonomers are used as reaction intermediate products in the preparation of other macromonomers, or directly as macromonomers for carrying out polycondensation or coupling reactions.

U.S. Pat. No. 3,689,593 describes graft copolymers in which the grafts are constituted of macromonomers with an OH, COOH or NH$_2$ end group, with which a diisocyanate, and then a functional vinylic monomer have reacted. These polymers are useful as filmogenic agents in compositions such as paints.

Other macromonomers in which the functional group is linked to the polymer group by an isocyanate group have been described particularly for their application in the dispersion and stabilisation of pigments. The following references shall most particularly be cited:

H. L. JAKUBAUSKAS in J. Coat. Techn., 58, n° 736, 71–82 (1986),
F. N. JONES in U.S. Pat. No. 4,070,388,
T. A. ASHE in U.S. Pat. No. 4,032,698,
D. R. THOMPSON in US Pat. No. 3,788,996, and
R. A. BRAUN in US Pat. No. 3,684,771.

The compounds described in the various documents above are constituted of various types of polymer chains functionalised with various end groups. All these macromonomers are obtained by functionalising a polymer chain with, for example, an —OH group with which a triisocyanate then reacts. A polymer chain is thus obtained which has two isocyanate end groups with which thiomalic acid may then be grafted. The dispersions carried out by the intermediate of these compounds are extremely resistant to flocculation, giving paintings in which they are incorporated increased covering capacity, brightness as well as improved resistance to loss of brightness. Moreover, the proportion of pigments may be increased in keeping the same degree of fluidity as with conventional dispersing agents. However, these products contain isocyanates which can prove to be a nuisance in a cosmetic formulation if there are residual isocyanate functions.

U.S. Pat. No. 5,298,585 describes chain end-functionalised polymers obtained by polymerisation in an aqueous medium in the presence of an amine-thiol-type chain transfer agent. However, the products described in this document are water-soluble polymers which contain a maximum of 80% and preferably 60% of unsaturated monomers other than of the acid type. It is a matter therefore of products whose polymer chain has an essentially hydrophilic character and which consequently have no surfactant character since the polymer chain which constitutes them is essentially hydrophilic. Even if a certain number of these polymers may have a dispersant character, this character is not at all linked to surfactant properties but simply to the polarity of the group fixed onto the polymer chain.

The present invention relates to the use of a family of products having the same advantages as those described above in what concerns their dispersant, stabilising and wetting potentials, but have in addition a surfactant character and furthermore are usable in dispersions for cosmetic use.

The invention also relates to the use of the same products as surfactants.

The invention also relates to a family of novel products which are limited in such a way as to take into account the fact that in the family, only the products obtained by radical polymerisation of a monomer in the presence of thiomalic acid were known, especially throughout the pieces of above-mentioned work by Y. YAMASHITA, Y. CHUJO et al.

More specifically, according to one of the essential characteristics, the invention relates to a functionalised polymer of the formula:

(P)—S—X—F  (1)

in which:
(P) is a hydrophobic polymer chain obtained by radical polymerisation of at least one monomer,
S represents sulphur,
X represents:
  a saturated or unsaturated linear or branched hydrocarbon chain having 1 to 6 carbon atoms and substituted with at least one COOH or NH$_2$ group, in the free or salified form;
  a peptide chain constituted of 2 to 4 amino acids, particularly natural amino acids;
F represents a COOH or NH$_2$ group, in the free or salified form,
with the exception of the ω-dicarboxylic macromonomers resulting from the radical polymerisation of a monomer in the presence of a chain transfer agent constituted of thiomalic acid.

According to a second aspect, the invention relates to a method of preparing the products described above.

According to this method, the functionalised polymer results from the radical polymerisation of at least one monomer in the presence of a thiol of formula H—S—X—F or a disulphide of formula F—X—S—S—X—F in which X and F have the meanings given above, said thiol or disulphide acting as a chain transfer agent during said radical polymerisation of said monomer(s) leading to the formation of the polymer chain (P) such as defined above, said thiol being different from thiomalic acid.

This method, at least when it uses a thiol as chain transfer agent, is a method which is directly inspired from that described in the pieces of work by YAMASHITA, CHUJO et al, cited above.

Due to its intermediate transformation into a thiol radical under the conditions of the reaction, it will also be possible for the disulphide to be used as chain transfer agent for preparing the functionalised polymers of the invention.

As it has been pointed out above, the synthesis of PMMAs functionalised with carboxylic acid groups is already known. YAMASHITA, CHUJO et al. have developed this type of macromonomers with the aim of copolymerising them by copolymerisation and thus forming graft copolymers (see particularly, E. J. GOETHALS, "Telechelic Polymers Synthesis and Applications" CRC Press, Inc, 169–179 (1989)).

The principle of this synthesis consists of radical polymerising methyl methacrylate in the presence of a transfer agent bearing acid functions, in this case thiomalic acid, under the conditions indicated in the reaction scheme (I) below:

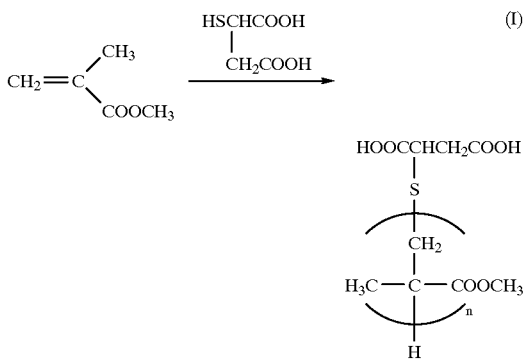

This reaction is carried out in a solvent medium, e.g. THF, in the presence of a radical polymerisation initiator, e.g. azobisisobutyronitrile (AIBN), at a temperature in the order of 60°C.

It will be possible for the functionalised polymers according to the invention to be advantageously prepared by an analogous method inspired from the reaction scheme (I) above by selecting the monomer(s) and the thiol according to the final product sought-after.

The radical polymerisation reaction of the monomer(s) will be carried out in a solvent medium in the presence of a radical polymerisation agent constituted of an organo-soluble initiator preferably selected from the family of azo initiators.

Azobisisobutyronitrile (AIBN) will be cited as an example of a preferred initiator.

The reaction takes place in a solvent medium.

The solvent or the mixture of solvents will be selected according to the nature of the monomer(s) to be polymerised and the thiol.

The solvent or the mixture of solvents will be selected according to the nature of the reagents. Preferably, it will be a matter of a solvent or a mixture of solvents which is capable of dissolving the whole of the reagents present, namely the monomers, the polymer formed, the initiator and the transfer agent.

The solvent may have an acidic character, acetic acid will be used for example; it may also have a basic character, e.g. dimethylethanolamine.

The reaction temperature will advantageously be between 30° C. and 120° C., but is to be adjusted according to the reagents present. It is easily understood that it depends on the nature of the initiator and the nature of the solvent.

The molecular mass of the functionalised polymer resulting from the process described above will be controlled in adjusting the amount of chain transfer agent introduced.

The proportions of initiator, transfer agent and monomer (s) may be calculated according to the classical relationship known for chain transfer:

$$\frac{1}{DPn} = \frac{1}{DPn_0} + Cs(\frac{S}{M})$$

wherein

S/M is the thiol/monomer molar ratio to be applied,

Cs is the transfer constant depending on the nature of the monomer(s), the transfer agent, the temperature and the solvent, DPn is the degree of polymerisation of the polymer that is desired to be synthesised, $DPn_0$ is the degree of polymerisation of the polymer that would have been obtained in the absence of a transfer agent.

Generally, in order to prepare functionalised polymers of the formula (I) described above, a thiol of formula H—S—X—F, wherein X and F have the meanings given above, will be used as chain transfer agent.

According to a variant of the method, it will be possible for a disulphide of formula F—X—S—S—X—F to be used as chain transfer agent, insofar as this disulphide is splitable into two F—X—S. radicals under the conditions of the radical polymerisation, these two radicals acting in a way which is analogous to what happens in the presence of the corresponding thiol H—S—X—F.

The thiols which are useful for preparing the compounds according to the invention are all the compounds of formula H—S—X—F in which:

X represents:
a saturated or unsaturated linear or branched hydrocarbon chain having 1 to 6 carbon atoms and substituted with at least one COOH or $NH_2$ group, in the free or salified form,
a peptide chain constituted of 2 to 4 amino acids, particularly natural amino acids, F represents a COOH or $NH_2$ group, in the free or salified form, with the exception of thiomalic acid.

The disulphides which are useful for preparing the functionalised polymers according to the invention are the disulphides of formula F—X—S—S—X—F wherein X and F have the meanings given above.

Particularly preferred functionalised polymers according to the invention are those in which the F—X part comprises at least one carboxylic function and at least one amine function, in the free or salified form.

As examples of such polymers, those in which the chain transfer agent is cysteine or homocysteine will be cited.

The functionalised polymers which result from the radical polymerisation of at least one monomer in the presence of cysteine acting as chain transfer agent will most particularly be cited.

Such a functionalised polymer following that it is in the free or salified form is of one of the formulae:

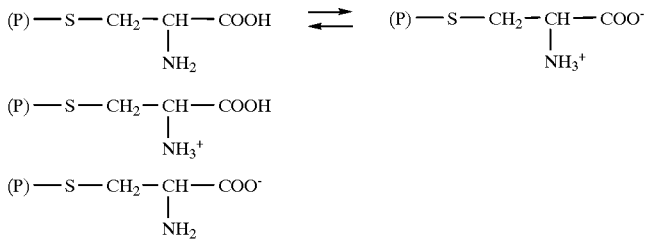

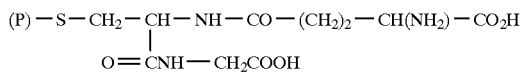

wherein (P) is a hydrophobic polymer chain resulting from the radical polymerisation of at least one monomer.

Functionalised polymers will also be cited which are of the formula:

$$(P)-S-CH_2-CH-NH-CO-(CH_2)_2-CH(NH_2)-CO_2H$$
$$|$$
$$O=CNH-CH_2COOH$$

in which the COOH and/or $NH_2$ functions may be free or salified and wherein (P) is a hydrophobic polymer chain obtained by radical polymerisation of at least one monomer.

Such polymers are obtained according to the method of the invention by radical polymerisation of at least one monomer which leads to the formation of the polymer chain (P) in the presence of glutathione acting as chain transfer agent.

The invention also relates to functionalised polymers obtained by radical polymerisation of at least one monomer in the presence of a peptide bearing at least one disulphide group and/or at least one thiol function.

Keratin hydrolysates will be cited as an example of a peptide bearing at least one thiol function.

Such products, due to the presence of at least one mobile hydrogen constituted by the hydrogen(s) of the thiol functions, will also be able to act as a chain transfer agent in the polymerisation leading to the formation of the polymer chain (P).

In all the polymers described above, it will be possible for the polymer chain (P) to be constituted of any hydrophobic polymer chain obtainable by radical polymerisation of at least one monomer.

It will therefore be a matter of both a chain constituted by radical polymerisation of one sole type of monomer and a chain constituted by radical polymerisation of a mixture of several different monomers.

An acrylic or vinylic monomer will advantageously be selected as monomer.

Amongst the acrylic monomers, the acrylates, methacrylates and ethylacrylates of a saturated or unsaturated C1 to C18 hydrocarbon group, particularly a linear, branched or cycle-containing allylic group, will most particularly be cited.

A preferred monomer according to the invention is methyl methacrylate. The polymer chain will then be constituted of methyl polymethacrylate (PMMA).

Amongst the vinylic monomers, styrene, alpha-methyl styrene, substituted styrenes, acrylonitrile, vinylic esters such as vinyl acetate will notably be cited.

Amongst the mixtures of monomers, mixtures of alkyl acrylate or methacrylate and allyl acrylate or methacrylate will be particularly cited, more particularly mixtures of methyl methacrylate and allyl methacrylate. The advantage of such monomers is that they lead to partially unsaturated polymer chains which enable obtaining specific properties of the polymers linked to the presence of these unsaturated bonds in the polymer chain.

As it has been seen above, the length of the chain may be adjusted by adjusting especially the proportion of thiol acting as chain transfer agent.

However, the most interesting compounds according to the invention are those for which the polymer chain (P) has a number average molar mass between 500 and 250,000.

All the above functionalised polymers, as well as those obtained by radical polymerisation of the same monomers in the presence of thiomalic acid, have interesting surfactant properties.

More specifically, all the functionalised polymers described above, as well as those obtained by radical polymerisation of at least one monomer such as defined above in the presence of thiomalic acid allow, due to their surfactant properties, lowering surface or interfacial tension, which is a matter of a liquid/liquid or a liquid/solid system.

In particular, these products, when placed in contact with a surface, enable lowering its surface tension.

These products, when placed in the presence of a particulate charge, also enable lowering the surface tension of said particles. This phenomenon of lowering the surface tension of the particles manifests itself as a wetting effect of the polymer with respect to said particle, by a dispersing effect of said particles when these particles are in suspension in a solvent, and by a stabilising effect of the dispersions of particles in a solvent.

For these different types of surfactant effects in the liquid/solid systems, the functionalised polymers may be salified or not.

The surfactant properties of the functionalised polymers described above may also manifest themselves in liquid/liquid systems.

As examples of such liquid/liquid systems, oil-in-water emulsions, water-in-oil emulsions may be cited as well as systems constituting starting systems intended to be polymerised for preparing a latex.

In the case of these liquid/liquid systems, the functionalised polymer may be either in the salified form or in the free form, but it will of preference in the salified form, which increases its emulsifying potential.

Hence, all the above functionalised polymers, as well as those obtained by radical polymerisation of at least one monomer such as defined above and leading to the formation of a hydrophobic polymer chain in the presence of thiomalic acid, have interesting surfactant properties enabling in particular their use as wetting agents and/or dispersing agents and/or stabilising agents for solid particle dispersions, enabling thus the formation of stable dispersions of particles.

Moreover, these same functionalised polymers, after neutralisation if need be of the COOH and $NH_2$ groups, have interesting surfactant properties, which enable in particular their use for preparing microdispersions of polymers in particular in the form of microlatex and microgels.

Hence, according to one of its aspects, the invention relates to the use of a functionalised polymer of formula:

(P)—S—X—F    (1')

in which:
- (P) is a hydrophobic polymer chain of number average molar mass between 500 and 250,000,
- S represents sulphur,
- X represents:
  - a saturated or unsaturated linear or branched hydrocarbon chain having 1 to 6 carbon atoms and substituted with at least one COOH or $NH_2$ group, in the free or salified form,
  - a peptide chain constituted of 2 to 4 amino acids, particularly natural amino acids,
- F represents a COOH or $NH_2$ group, in the free or salified form, or of a polymer resulting from the radical polymerisation of at least one monomer leading to a hydrophobic polymer chain in the presence of a peptide bearing at least one disulphide group and/or at least one thiol function, such as a keratin hydrolysate, as surfactant.

The applicant has most particularly demonstrated the surfactant properties of the functionalised polymers defined above by studying their effect on the surface tension of a solid surface or a particle.

The applicant has also demonstrated their wetting character as well as their dispersing and stabilising properties of dispersion of particles.

The applicant's studies have led, for the various functionalised polymers of the family, according to the nature of the medium in which it is desired to disperse the powder as well as the nature of the powder:
- on the one hand, to the determination of the adsorption yield of the functionalised polymer defined as the amount of functionalised polymer <<fixed>> with respect to the amount employed. <<Fixed>> functionalised polymer meaning the functionalised polymer adsorbed by the physical bonds on the surface of the solid particle,
- and on the other hand, to the determination of the efficiency of the surfactant as a wetting agent and/or dispersing agent and/or stabilising agent.

The applicant's studies have in particular brought about the demonstration of the existence of a plateau in the curves, known as adsorption isotherms, which represent the rate of adsorption of the functionalised polymer according to the initial concentration of the functionalised polymer at a given temperature.

The efficiency of the wetting agent and/or dispersing agent and/or stabilising agent is characterised by the minimal amount of functionalised polymer to be employed in order to reach the adsorption isotherm plateau and to cover all the surface of the particle.

The applicant's studies have led to the demonstration of the significant reduction of the wettability parameter of the solid particles. This effect demonstrates the wetting character of the products according to the invention.

Hence, the invention also relates to the use of the surfactants defined above as a wetting agent of a solid surface or a solid particle.

The applicant has also demonstrated the significant reduction of the amount of aggregates formed between the particles and/or the significant reduction in their size in the presence of functionalised polymer in the medium. This effect demonstrates the dispersant character of the products according to the invention.

The invention also relates therefore to the use of the functionalised polymers of the family (1') as well as to the polymers resulting from the radical polymerisation of at least one monomer leading to the formation of a hydrophobic polymer chain in the presence of a peptide bearing at least one disulphide group and/or at least one thiol function, such as a keratin hydrolysate, as dispersing agents of solid particles in an organic medium.

The applicant has also demonstrated that the functionalised polymers defined above constituted remarkable stabilising agents of dispersions of solid particles in organic media and enabled in particular obtaining dispersions whose supernatant does not become limpid before at least 24 hours for the contents of polymers which correspond to the plateau of the adsorption isotherm.

The solid particles may be of any type and have advantageously dimensions between a few nanometers and a few millimeters, preferably between 50 nm and 100 μm.

It may also be a matter in particular of inorganic particles, particularly of metallic oxide particles, for example $TiO_2$, $SiO_2$, $Al_2O_3$, iron oxides such as goethite, haemetite or magnetite.

It may also be a matter of metallic oxide particles covered with organic colorant molecules.

It may also be a matter of organic particles, for example of the rosinate type, co-precipitated with an organic colorant.

The organic medium used for carrying out the treatment of the solid particles may be any solvent of the polymer chain (P).

As an example, when the polymer chain is constituted of PMMA, the solvent will advantageously be selected from the esters such as methyl, ethyl, butyl or amyl acetates, ketones such as acetone, methyl ethyl ketone or cyclohexanone, chlorinated solvents such as chloroform or dichloromethane, or others such as toluene, and acetic acid.

It will also be possible to use mixtures of a solvent of PMMA with a non-solvent of PMMA in proportions which keep these sequence soluble, such as, for example, a butyl acetate/ethanol or isopropanol mixture which contains at least 50% butyl acetate.

All the functionalised polymers described above have a wetting and dispersing effect.

The stabilising effect of the dispersion itself is only sensitive as from a number average molecular mass of the polymer which is greater than 1,000, preferably between 5,000 and 150,000.

However, it will easily be understood that the values depend upon both the nature of the filler to be dispersed as well as that of the polar head of the functionalised polymer.

The invention can be applied most particularly to the dispersion of titanium oxide particles, particularly particles of dimensions between 50 nm and 1 μm.

In practice, the adsorption yield is determined in the following way: a mass $m_S$ of solution of initial polymer concentration Ci is placed in contact with a mass $m_C$ of particles of specific surface S. After adsorption, and after the removal of the particles by centrifugation, the new concentration (Ce) of the solution is determined. The yield (r) is given by the formula:

$r=(C_i-C_e)/C_i \times 100 (\%)$

The rate of adsorption (t) itself is given by:

$t=[(C_i-C_e) \times m_S]/m_C \times S$

The dispersability is evaluated from the measurements of the sizes of the particles, for example with the aid of an apparatus of the Coulter LS130 type.

A particular advantage of the functionalised polymers used as dispersants according to the invention is that they lead to stable dispersions.

Hence, according to one of its aspects, the invention relates to stable dispersions of solid particles in a solvent, or a mixture of solvents, in which the dispersing agent is a functionalised polymer of formula (1') such as defined above, or a polymer resulting from the polymerisation of at least one monomer leading to a hydrophobic polymer chain in the presence of a peptide bearing at least one disulphide group and/or at least one thiol function, such as a keratin hydrolysate, said solvent or mixture being a solvent of said polymer chain.

The stabilisation of the dispersion is appreciated either by measuring the speed of sedimentation of the suspensions with time, or by following the variations of the absorbance of the supernatant in terms of the duration of the centrifugation.

One advantage of the dispersions according to the invention is that, when a decantation is produced with time, the deposit formed remains easily redispersable in the medium after stirring, the polymer totally covering the surface of the particle, which thus prevents its aggregation.

Another advantage of the dispersions according to the invention is that, when they are dried at room temperature, the powder recovered can be easily redispersed later in the solvent.

According to another of its essential characteristics, the invention also relates to any composition which contains the dispersions described above. It relates most particularly to the compositions which contain dispersions of pigments intended for the cosmetics field.

The functionalised polymers usable as wetting agents and/or dispersing agents and/or stabilising agents of particles according to the invention are advantageously selected from the functionalised polymers resulting from radical polymerisation of at least one monomer leading to a polymer chain in the presence of a thiol F—X—SH or a disulphide of formula F—X—S—S—X—F in which X and F have the meanings given above, said thiol or disulphide acting as chain transfer agent during said radical polymerisation, said monomers leading to the formation of the polymer chain (P) such as defined above.

It may particularly be a matter of polymers defined above in which the F—X part, F and X having the meanings given above, comprises at least one carboxylic function and at least one amine function, in the free or salified form.

It may also particularly be a matter of the functionalised polymer of the formula:

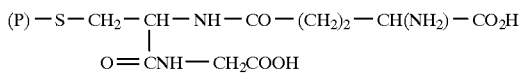

in which the COOH and/or $NH_2$ functions are free or salified, and in particular of the functionalised polymer obtained by radical polymerisation of a monomer leading to the polymerised chain such as defined above in the presence of a chain transfer agent constituted by glutathione.

It will also be possible to advantageously use the functionalised polymers in which the hydrophobic polymer chain is obtained by radical polymerisation of at least one monomer in the presence of cysteine or homocysteine acting as chain transfer agent.

It will also be possible to use the functionalised polymers obtained by radical polymerisation of at least one monomer in the presence of a peptide bearing at least one disulphide group and/or at least one thiol function, such as a keratin hydrolysate.

For this use, the polymer chain advantageously results from the radical polymerisation of at least one acrylic or vinylic monomer.

According to another of its aspects, the invention also relates to the use of the functionalised polymer of formula:

(P)—S—X—F            (1')

such as defined above, or of a polymer resulting from the radical polymerisation of at least one monomer leading to a hydrophobic polymer chain in the presence of a peptide bearing at least one disulphide and/or thiol function, such as a keratin hydrolysate, as surfactant having an emulsifying role, if need be after neutralisation of the COOH or $NH_2$ groups.

All the products described above as wetting agents and/or dispersing agents and/or stabilising agents of dispersions of particles may also be used as surfactants having the emulsifying role after neutralisation, if need be, of the COOH or $NH_2$ groups.

The invention also relates to the use of the same polymers for the preparation of microdispersions of polymers:
- either in aqueous or aqueous-alcohol media (as we shall refer to as microlatex),
- or in organic media (which we shall refer to as microgels) thus demonstrating their surfactant properties.

For this application, from the functionalised polymers defined above, those having a number average molecular mass ($M_n$) lower than about 20,000, preferably between 500 and 10,000, will be preferably selected.

Due to their surfactant properties, the useful functionalised polymers according to the invention can easily form micellar solutions in aqueous media, after neutralisation of their acid and/or basic functions.

These micellar solutions can then be used in the formulation of latex, in particular a cross-linked latex, notably a cross-linked latex of small sizes referred to as microlatex (10–150 nm). These microlatexes may be prepared by any polymerisation method in emulsion in the presence of an organo or hydrosoluble initiator, as it has been shown by W. FUNKE with saturated or unsaturated polyesters, particularly in:

"Emulsifying properties of saturated polyesters" H. BAUMANN, B. JOOS, W. FUNKE, Makromol. Chem., 187, 2933 (1986), "Saturated polyesters as emulsifiers for emulsion copolymerization of unsaturated polyester resins with styrene" H. BAUMANN, B. JOOS, W. FUNKE Makromol. Chem., 190, 83–92 (1989), "Reactor Microgels by Self-emulsifying Copolymerization of Unsaturated Polyester Resins with Acrylic and Methacrylic Esters" Makromol. Chem., 184, 755–762 (1983) M. MIYATA, W. FUNKE "Reactive Microgels by Emulsion Polymerization of Unsaturated Polyester Resins" Y.-Ch. YU, W. FUNKE Die Angewandte Makromol. Chem., 103, 187–202 (1982), "Surfactant Properties of Unsaturated Polyesters" Y.-Ch. Yu, W. FUNKE Die Angewandte Makromol. Chem., 103, 203–215 (1982).

The advantage of these microlatexes is that:
they give very stable polymer dispersions,
once dry, powders of extremely high specific surfaces are obtained;
they enable preparing microgels whose advantages are illustrated in the examples;
they also enable forming films (according to the nature of the polymer and the solvent).

These microlatexes may then advantageously be used for the preparation of microgels.

These microgels are obtained from the above cross-linked microlatexes, either by transferring the particles constituting the dispersion in a solvent after prior drying the dispersion, or by azeotropic removal, or by mixing with a solvent and then distilling the water.

As examples of solvents, the aromatic solvents will be cited, the chlorinated solvents such as chloroform or methylene chloride, ketones and esters such as $C_2$ to $C_4$ alkyl acetates, more particularly butyl acetate and ethyl acetate.

The microgels of the invention prove to be particularly useful in the cosmetic and paints fields, where they enable adjusting the rheological characteristics. It is in fact possible to mix the microgels with formulations based on nitrocellulose of high dry extract, without especially increasing the viscosity of the system which results from it.

The fact that the products are compatible with the nitrocellulose dissolved in butyl acetate giving a transparent and bright film enables envisaging their use for making varnishes, particularly nail varnishes.

More specifically, the use of the microgels of the invention in the formulations of varnishes and particularly nail varnishes has the following advantages:
it enables improving the rheological properties which enables, in particular, avoiding the precipitation of the pigments, and an improvement of the reproducibility of these properties. This enables, in particular, to appreciably decrease, even to do away with, the amount of organophilic clays generally used to this end but whose disadvantages are well-known,
it enables increasing the dry extract of the film constituted by the varnish without meaning appreciably increasing the viscosity of the varnish;
it confers more brightness to the film,
it reinforces the thixotropic effect brought about by the organophilic clay in acetate medium.

The weight proportion of microgel according to the invention, in the final composition of the varnish, may rise up to about 30%, for example in the case where it would be sought to lower, even to do away with the quantity of nitrocellulose. However, in general it is preferred to use proportions between about 1 and 20% by weight.

As it arises from the preceding account, the dispersions of particles described above as well as the microgels may advantageously be introduced in different compositions, especially cosmetic compositions and in particular nail varnishes.

Hence, according to other aspects, the invention also relates to compositions, especially cosmetic compositions which contain functionalised polymers according to the invention.

In particular, these cosmetic compositions are intended for the care or the make-up of the nails and contain dispersions of particles, particularly pigments, described above.

These compositions may further contain nitrocellulose.

The invention also relates to microlatexes and microgels described above as well as the compositions, especially the cosmetic compositions containing them.

It relates most particularly to the compositions which further contain nitrocellulose, particularly nail varnishes.

More generally, it also relates to the use of the polymers of the family (1') as well as to polymers resulting from the radical polymerisation of at least one monomer such as defined above and leading to a hydrophobic polymer chain in the presence of a peptide bearing at least one disulphide group and/or at least one thiol function, such as keratin hydrolysates, for the preparation of a composition, particularly a composition of the paint type, or a food composition, a phytosanitary composition or a cosmetic composition, particularly a cosmetic composition intended for the care or the make-up of the nails and more particularly a nail varnish.

The invention relates most particularly, as this arises from the preceding account, to the use of the polymers defined above for the preparation of compositions which contain solid particles in suspension, particularly pigments, in which said functionalised polymer is placed in the presence of said solid particles, especially said pigments, in order to facilitate their dispersion in the composition.

In the compositions described above, the amount of functionalised polymers used is advantageously between 2% and 7% by weight with respect to the total weight of the solid particles dispersed in the composition.

In the compositions defined above, the functionalised polymer is advantageously comprised in polymer microdispersions, especially microgels or microlatexes, the functionalised polymer being like it has been shown before used as a surfactant for the preparation of these microgels or microlatexes.

The amount of microdispersions of polymers, microgels or microlatexes is advantageously between 1% and 20% by weight with respect to the total weight of the composition.

According to a last aspect, the invention relates, as this arises from the preceding account, to cosmetic compositions, and, most particularly, to cosmetic compositions intended for the care or the make-up of the nails, which contain functionalised polymers defined above, in particular comprised in microdispersions, especially microlatexes or microgels.

It relates most particularly to cosmetic compositions which further contain nitrocellulose.

EXAMPLES

Examples which are purely illustrative of the invention are given below.

These examples are grouped in the following parts:
I: for the synthesis (examples I.1.a, I.1.b, I.1.c, I.1.d, I.2, I.3, I.3.a, I.3.b and I.4)
II: for the demonstration of the wetting effect
III: for the demonstration of the dispersing effect and/or the stabilising effect
IV: for the demonstration of the formation of micelles and their application in the preparation of microdispersions
V : for the applications in the cosmetics field.

These examples are given with reference to the annexed Figures which demonstrate the dispersing and stabilising properties of the exemplified products, more specifically:

FIGS. 1 to 4 are given with reference to Example III.1 and more specifically relate to:

FIG. 1: the isotherm and the yield of adsorption of functionalised polymer obtained in Example I.1.b on a $TiO_2$ powder in a butyl acetate medium.

FIGS. 2a, 2b, 2c, 2d, 2e, 2f: the results obtained by measuring the dispersability, with a COULTER LS130, of the same powder in the same medium for various initial polymer concentrations.

FIG. 3: the sedimentation speed of the same powder in the same medium, in the presence and in the absence of functionalised polymer.

FIG. 4: the absorbance of the suspension with centrifugation time for the non-treated powder and in the presence of various concentrations of functionalised polymer.

FIGS. 5 to 7 are given with reference to Example III.2 and more specifically relate to:

FIG. 5: the isotherm and the yield of adsorption of the functionalised polymer obtained in Example I. 1.c on a TiO, powder in a butyl acetate medium.

FIGS. 6a, 6b, 6c, 6d, 6e, 6f: the results obtained by measuring on a COULTER LS130 the dispersability of the same powder in the same medium for various initial polymer concentrations.

FIG. 7: the absorbance of the suspension with centrifugation time for the non-treated powder and in the presence of various concentrations of functionalised polymer.

Figure 10:
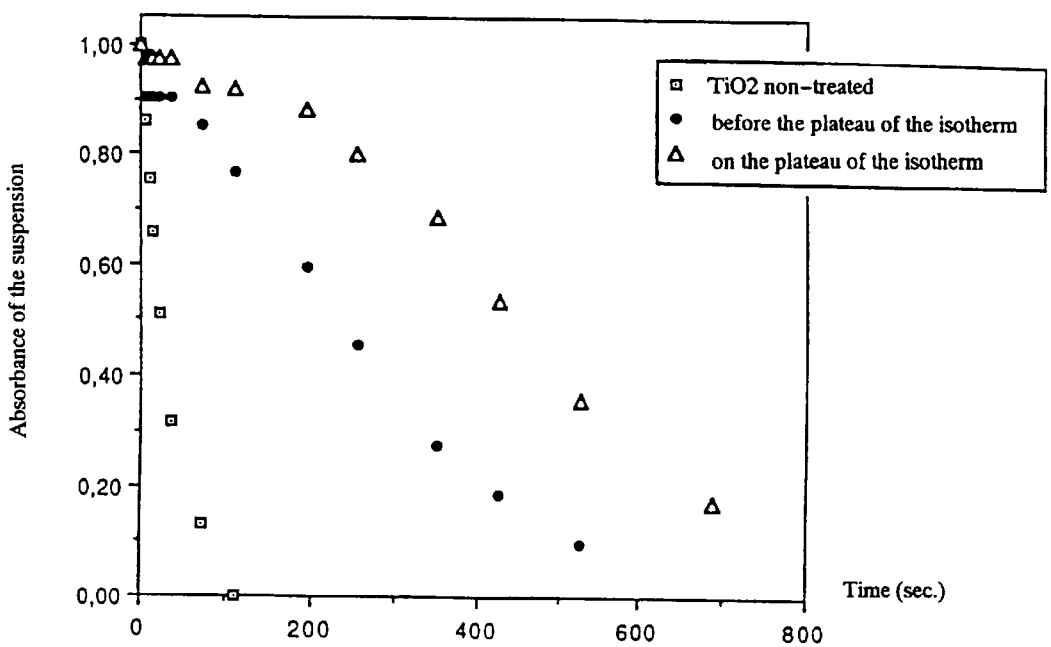
Figure 11:
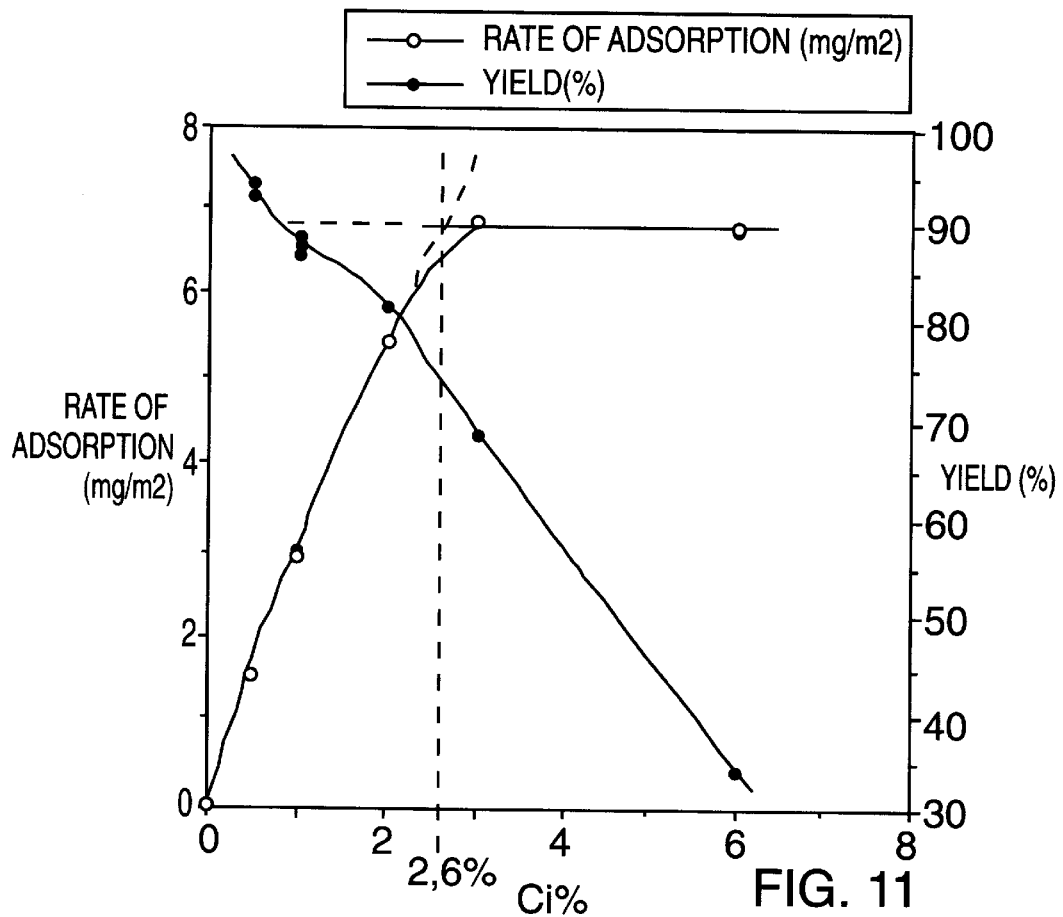

FIG. 10 gives, for the same system, the absorbances of different suspensions in the presence and the absence of functionalised polymer FIG. 11 is given with reference to Example III.5 and presents the isotherm of adsorption of the product obtained in Example I.4 on a $TiO_2$ powder in a butyl acetate medium.

Figure 12:
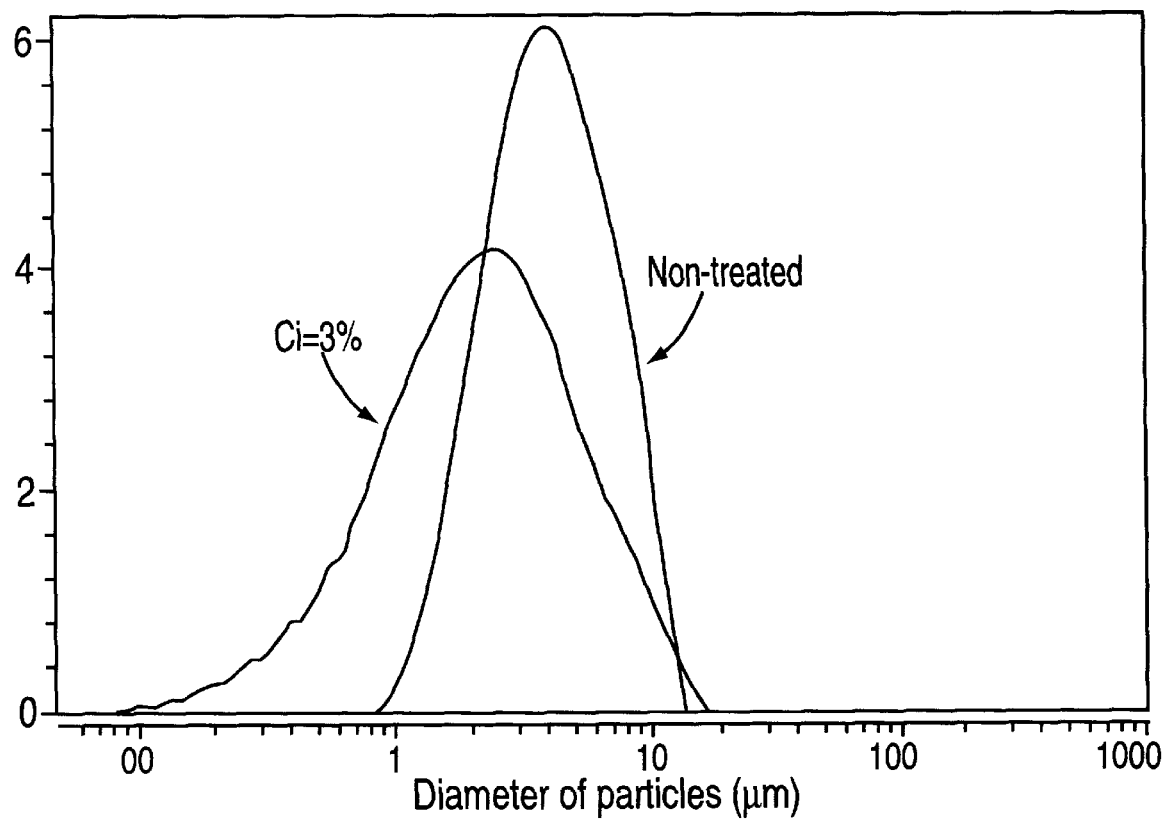

FIG. 12 is given with reference to Example III.6 and presents the results obtained by measuring on the COULTER LS130 in the presence and in the absence of functionalised polymer.

Figure 13:
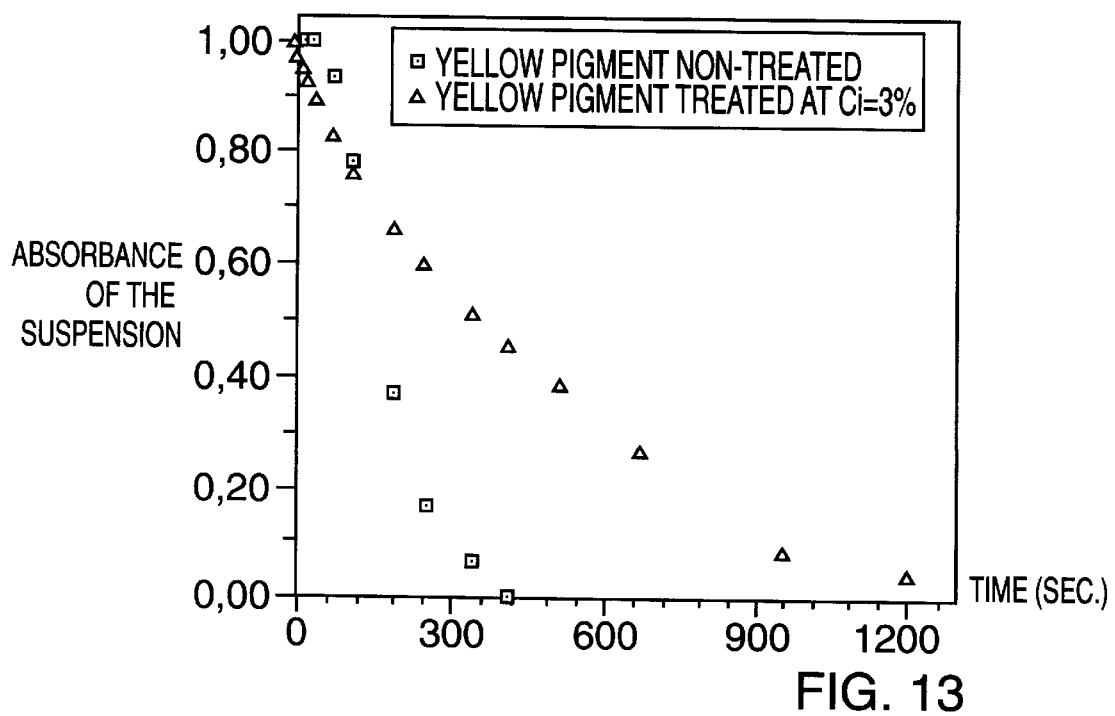

FIG. 13 given with reference to Example III.6 gives the absorbance of a suspension of alumina pigment covered with an organic colorant in the absence and in the presence of functionalised polymer obtained in Example I.4

I - Examples of syntheses of functionalised polymer

I.1 - Thiomalic acid-functionalised PPMA

The proportions of initiators and monomer transferers to be employed have been calculated from the results of YAMASHITA, CHUJO et al. according to the formula:

$$\frac{1}{DPn} = \frac{1}{DPn_0} + Cs(\frac{S}{M})$$

I.1.a - Preparation of a functionalised polymer of theoretical Mn of 1,000

In order to prepare a functionalised polymer having a theoretical $M_n$ of 1,000:1.58 g of AIBN, 33.47 g of thiomalic acid and 100 g of MMA are dissolved in 350 ml of THF (tetrahydrofuran).

This solution is placed in a double cased reactor equipped with a stirring anchor, a condenser and a nitrogen circulation, and is heated at 60° C. for 2 hours 30 minutes.

The mixture collected is precipitated in petroleum ether once or twice so as to remove the remains of MMA, AIBN and its decomposition products. Dried, it is then dissolved in acetone and reprecipitated several times in water (twice) so as to get rid of the thiol and the disulphide. A determination of the acid functions before and after precipitation shows the efficiency and consequently the necessity of this first purification.

The number molecular mass is:

1030 (determined by vapour pressure osmometry)

960 (determined by GPC, gel permeation chromatography)

I.1.b - Preparation of a thiomalic acid-functionalised polymer having a theoretical Mn of 8,000.

The proportions to be employed of initiator and monomer transferer have been calculated from the results of YAMASHITA CHUJO et al. according to the formula:

$$\frac{1}{DPn} = \frac{1}{DPn_0} + Cs(\frac{S}{M})$$

Carried out as in Example I.1.a with the following quantities of reagents:

100 g of MMA
3.6 g of thiomalic acid
1.36 g of AIBN
250 ml of THF
the reaction temperature is 60° C. and the duration of polymerisation is 3 hours 30 minutes.
the purification is carried out as in Example I.1.a.
the molecular mass measured by GPC is Mn=7,000

I.1.c- Preparation of a thiomalic acid-functionalised PMMA of theoretical Mn 1,500

Carried out on the same calculation basis as that for the product of Example I.1.a using the following operation conditions:

100 g of MMa
22.2 g of thiomalic acid
1.58 g of AIBN
300 ml of THF
T=60° C.
Duration of polymerisation: 2 hours 30 minutes
The results are the following:
Mn=1390 determined by GPC
Mn=1270 determined by vapour pressure osmometry.

I.1.d - Preparation of a thiomalic acid-functionalised PMMA of theoretical Mn 15,000

Carried out as in Example I.1.c above with the following operating conditions:

100 g of MMA
1.61 g of thiomalic acid
1.36 g of AIBN
315 g of THF
T=60° C.
Duration of polymerisation: 4 hours 15 minutes
the number average molecular mass determined par GPC is 12,300.

I.2 - Thiomalic acid-functionalised poly (methyl methacrylate-co-allyl methacrylate)

0.32 g of AIBN, 0.69 g of thiomalic acid, 4 g of allyl methacrylate and 16 g of MMA are dissolved in 70 ml of THF.

this solution, placed in a double cased reactor equipped with a stirring anchor, a condenser and a nitrogen circulation, is heated at 60° C. for 2 hours 30 minutes.

The mixture collected is precipitated in petroleum ether. Dried, it is then dissolved in acetone and reprecipitated in water (twice).

The number molecular mass is:

1420 (determined by GPC)
1500 (determined by VPO, vapour pressure osmometry).

I.3 - Cysteine-functionalised PMMA

I.3.a - PMMA of theoretical Mn equal to 15.000.

2.19 g of cysteine are dissolved in 50 g of water 350 g of acetic acid are then progressively added.

the solution obtained is placed in a reactor (apparatus similar to those of the preceding Examples).

0.63 g of AIBN are dissolved in 40 g of MMA.

The whole is added to the above solution.

The whole is heated for 60° C. for 4 hours.

The mixture collected is precipitated in n-butanol so as to remove the remains of MMA, AIBN and its decomposition products.

Dried, optionally washed with water, it is then dissolved in acetone and reprecipitated twice in water so as to rid it of thiol and disulphide.

The number molecular mass determined by GPC is Mn=14,800.

I.3.b - PMMA of theoretical Mn equal to 7,500 functionalised on the chain end with cysteine Carried out as in Example I.3.a. with proportions calculated in function of the results of this synthesis.

The operating conditions are the following:

40 g of MMA
4.38 g of cysteine
0.63 g of AIBN
370 g of acetic acid
80 g of water
T=60° C.
Duration of polymerisation: 6 hours The functionalised polymer has an Mn determined by GPC of 7,550.

I.3.c - PPMA of Mn equal to 3380 functionalised on the chain end with cysteine

Carried out as in Examples I.3.a and I.3.b under the following operation conditions:

40 g of MMA
8.76 g of cysteine
0.63 g of AIBN
320 g of acetic acid
80 g of water
T=60° C.
Duration of polymerisation: 5 hours.

I.4 - Glutathione-functionalised PMMA 2.78 g of glutathione are dissolved in 40 g of water 160 g of acetic acid are then added progressively.

the solution obtained is placed in a reactor similar to that of the preceding Examples 0.32 g of AIBN are dissolved in 20 g of MMA.

The whole is heated at 60° C. for 4 hours 30 minutes.

The mixture collected is precipitated in n-butanol.

Dried, optionally washed with water, it is then dissolved in acetone and reprecipitated twice in water.

the number molecular mass determined by GPC is Mn=25,100.

II - Demonstration of the wetting effect

The modification of the surface energy is estimated by the STEVENS test such as it is described by P. STEVENS, L. GYPEN, R. JENNEN-BARTHOLOMEUSSEN in "Wettability of powders". Farmaceutisch Tijdschrift voor Belgïe; 51e jaargang, nummer 2, maat, April 1974

Before treatment, the $TiO_2$ has a wettability greater than 73.6 mJ/m$^2$ and therefore a marked hydrophilic character. After adsorption of the functionalised polymer (Ci=3%), a clear reduction on the wettability parameter to a value of about 51.5 mJ/m2 is observed with the functionalised polymers described in parts I.1.a and I.1.b.

III.- Demonstration of the dispersing effect and/or the stabilising effect of dispersions of powders of the functionalised polymers.

III.1 Dispersion of a titanium powder.

A PMMA functionalised on the chain end with an —SCH(COOH)(CH$_2$COOH) group, obtained according to Example I.1.b, is used as functionalised polymer.

The solvent used is butyl acetate.

The powder used is a titanium oxide powder of average diameter 200 nm and a specific surface of 10 m$^2$/g.

The functionalised polymer is placed in solution in butyl acetate at various concentrations. 3g of $TiO_2$ to 10 g of solution are then added. Stirring is then continued for 24 hours. The determination of the adsorption isotherms (adsorption rate in terms of the initial polymer concentration at 20° C.) enables obtaining the maximum adsorption rate as well as the yield as FIG. 1 shows.

Figure 1:
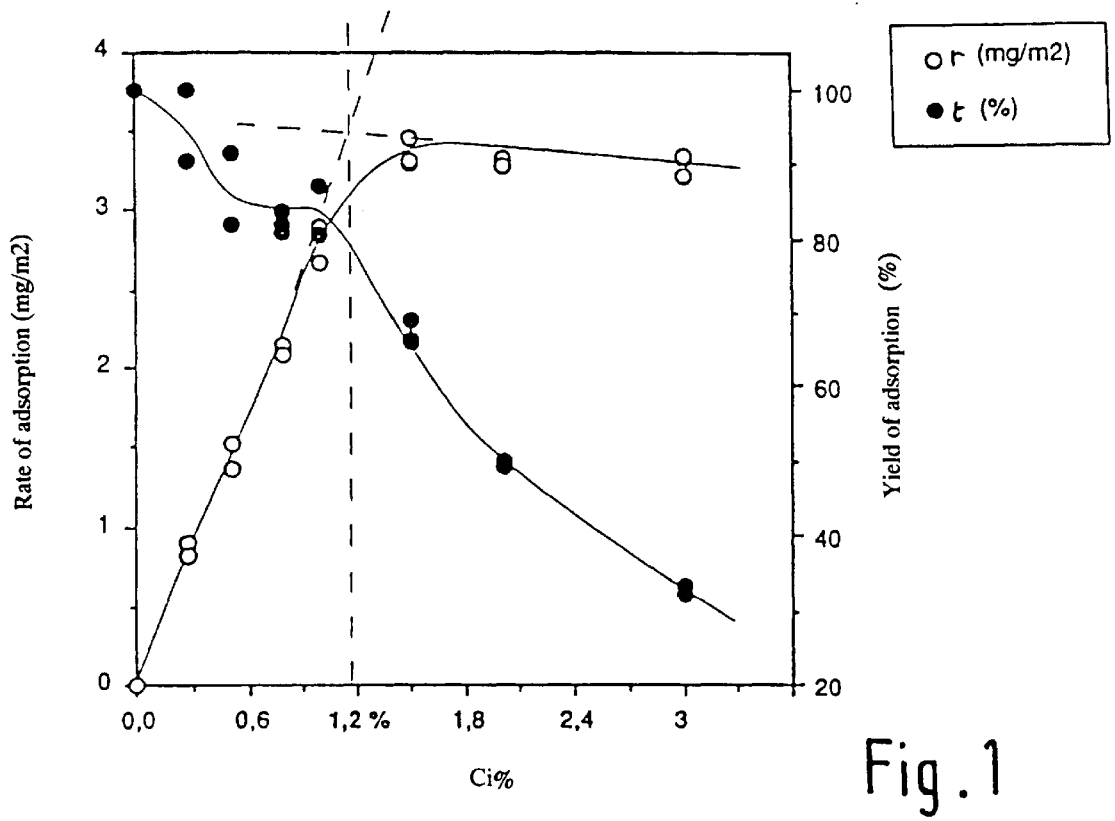

FIG. 1 gives the rate of adsorption (t) and the yield of adsorption (r) in terms of the initial concentration of functionalised polymer, expressed in percentages by mass. The yield r is given by the relationship:

$$r=(Ci-Ce)/Ci\times100(\%)$$

wherein Ci represents the initial concentration of functionalised polymer and Ce the concentration of the solution after placing the solution in contact with the solid particles and separating the solid particles by centrifugation.

The rate of adsorption is given by $$t=[(Ci-Ce)m_S]/m_C S$$

wherein $m_S$ is the mass of the solution and $m_C$ the mass of $TiO_2$ of specific surface S.

In the present case:

$m_S$=10 g
S=10 m$^2$/g
$m_C$=3 g

The line of the curve of FIG. 1 giving the rate of adsorption in terms of the initial concentration Ci of the functionalised polymer at 20° C. (adsorption isotherm) clearly shows the existence of a plateau whose start is determined by a line of the tangents as indicated in FIG. 1.

In the particular case of this Example, the start of the plateau read on the curve corresponds to an initial concentration of functionalised polymer of 1.2% by mass.

The calculation according to the relationship above shows that this concentration corresponds to the adsorption of 40 mg of polymer per g of $TiO_2$.

The dispersability is evaluated from the measurements of the sizes of the particles with the aid of the COULTER LS130.

FIGS. 2a to 2f give the granulometric analyses of the $TiO_2$ at various stages of treatment for the same example as the adsorption isotherm. The functionalised polymer enables considerably reducing the aggregates until they disappear when the covering of the $TiO_2$ is total (i.e. for the initial polymer concentrations corresponding to the plateau of the isotherm).

For this type of example, a very good dispersing agent must reduce the quantity of aggregates to a value lower than 1% or at least considerably reduce their size.

Figure 3:
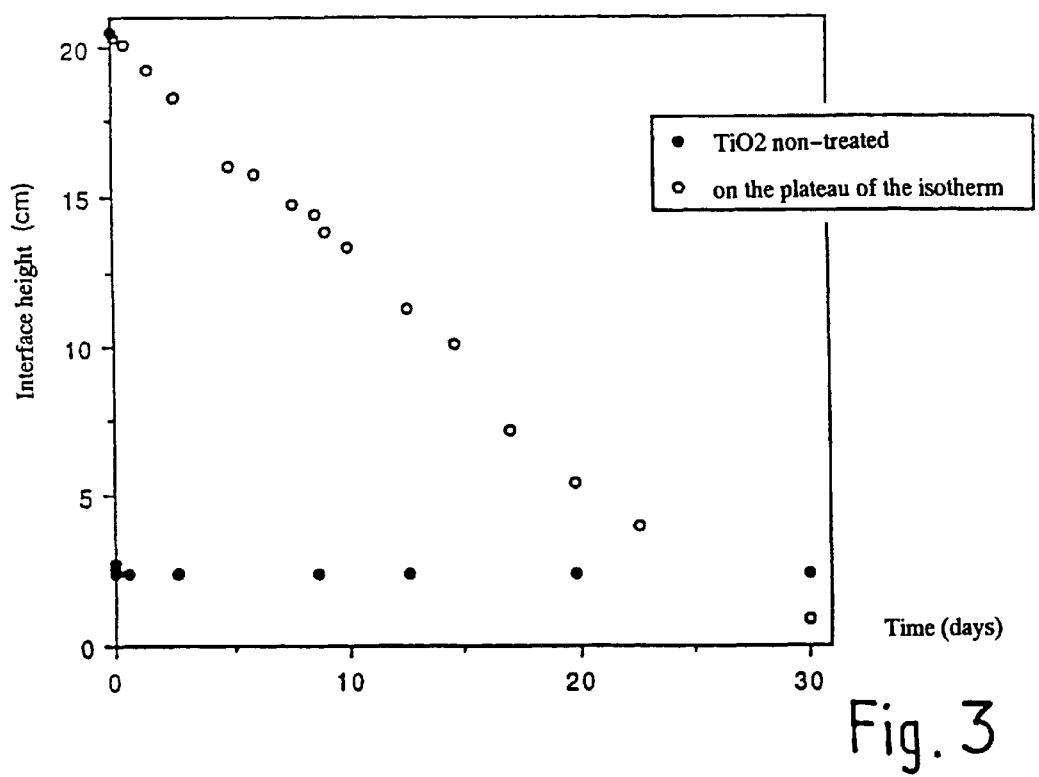
Figure 2A:
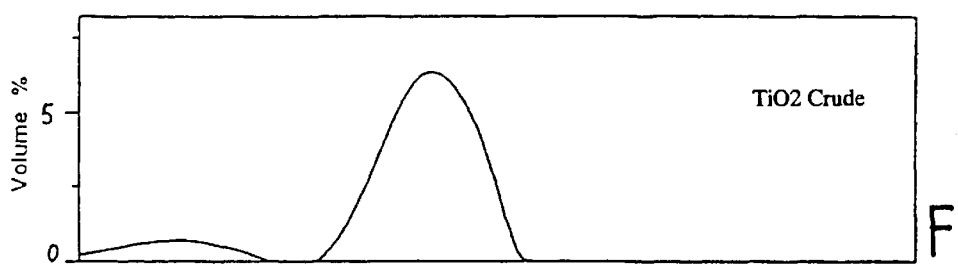
Figure 2B:
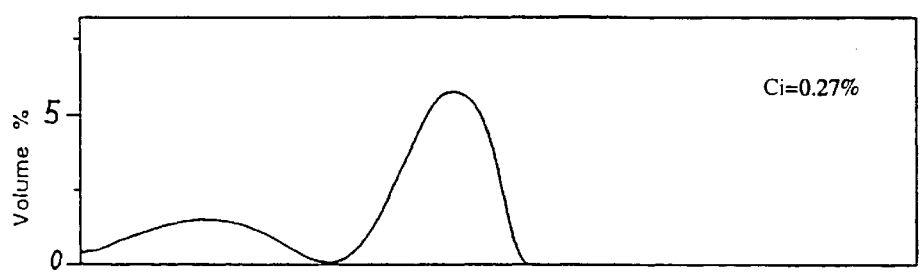
Figure 2C:
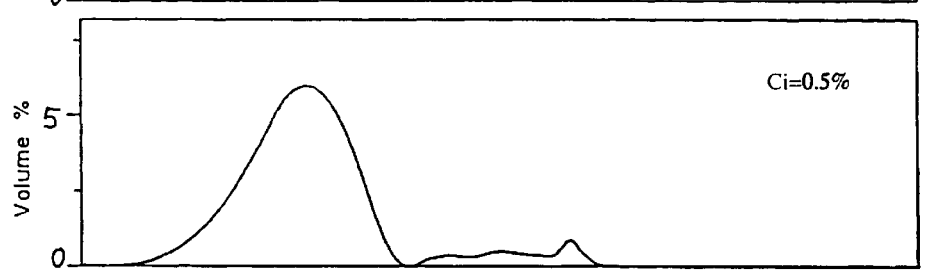
Figure 2D:
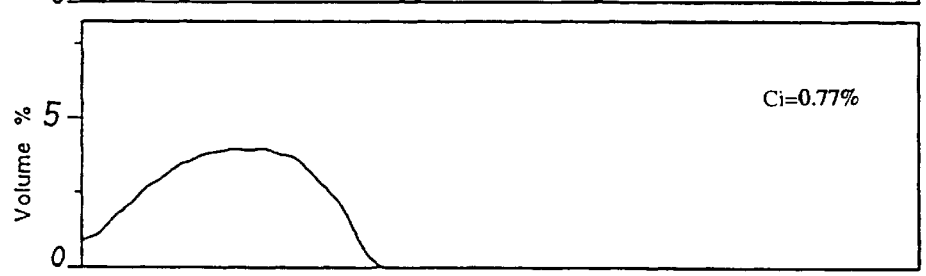
Figure 2E:
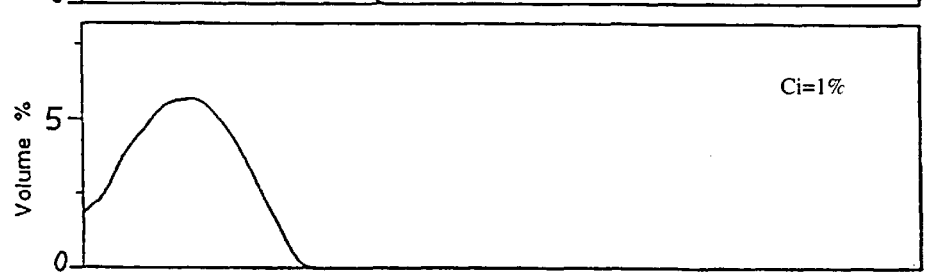
Figure 2F:
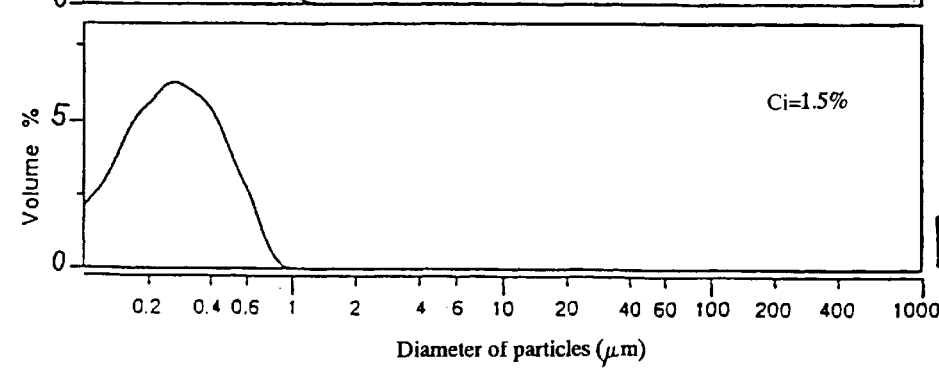

The stabilisation is determined:

either by the speed of sedimentation of the suspensions in tubes in terms of time, FIG. 3 gives the height of the interface in terms of the time for a non-treated $TiO_2$ powder as well as for the powder treated by the functionalised polymer used at a concentration Ci=3% corresponding to the plateau of the isotherm.

or by varying the adsorbance of the supernatant in terms of the duration of the centrifugation of 120 rpm/mn$^2$ (Shimadzu SA-CP3). (FIG. 4).

Figure 4:
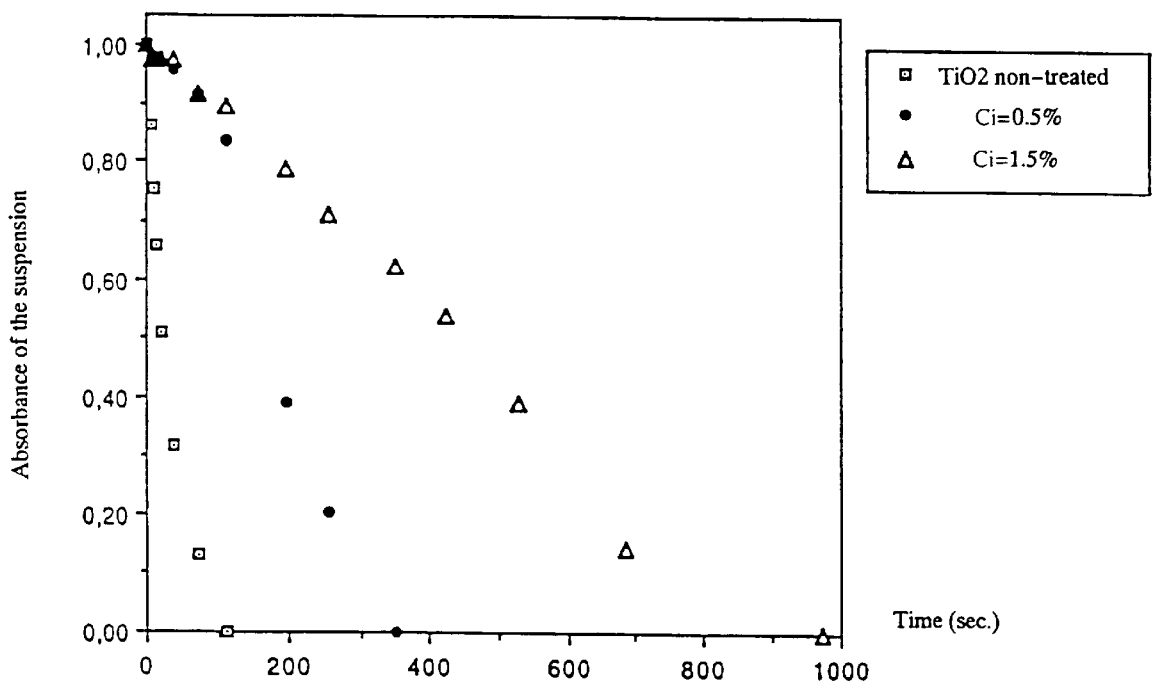

FIG. 4 gives the absorbance of the suspensions in terms of the time respectively for the non-treated $TiO_2$ suspensions as well as for concentrations Ci of 0.5 % (before the isotherm plateau) and 1.5% (on the isotherm plateau).

When there is a decantation with time, the deposit formed remains easily redispersable in the medium after a more or less long period of stirring. The polymer totally covering the surface preventing the aggregation of the pigment.

III.2 - Dispersion of a titanium oxide powder.

Carried out as in Example III.1, using methyl polymethacrylate functionalised on the chain end with a —SCH(COOH)—CH$_2$COOH) group, obtained according to Example I.1.c, in order to disperse in a butyl acetate medium a $TiO_2$ powder of 200 nm average diameter and 10 m$^2$/g specific surface.

Figure 5:
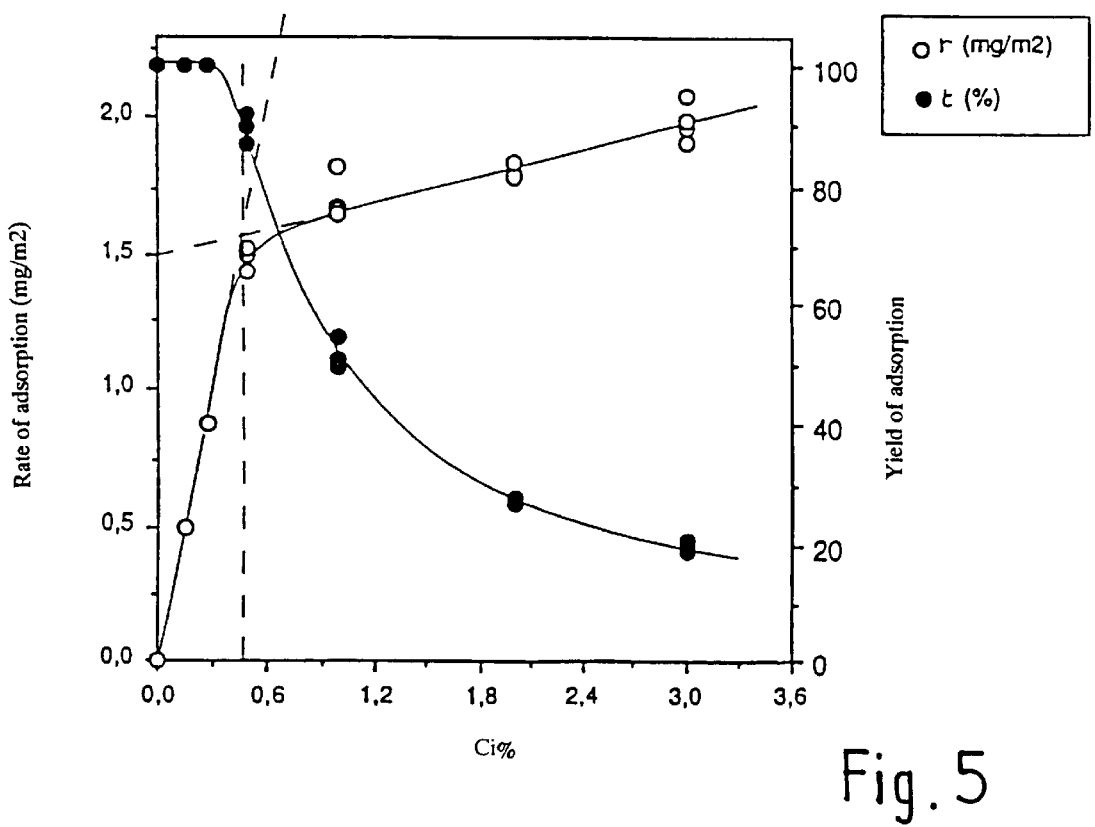
Figure 6A:
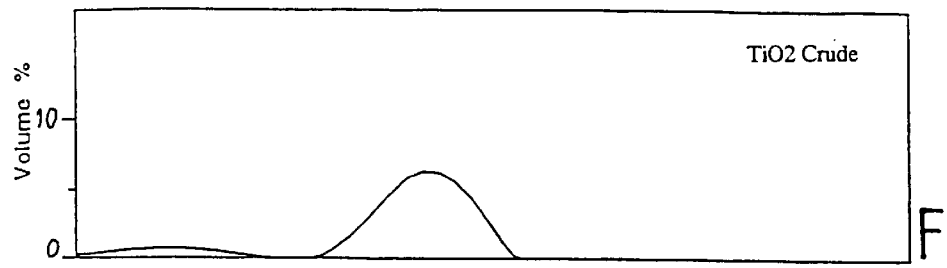
Figure 6B:
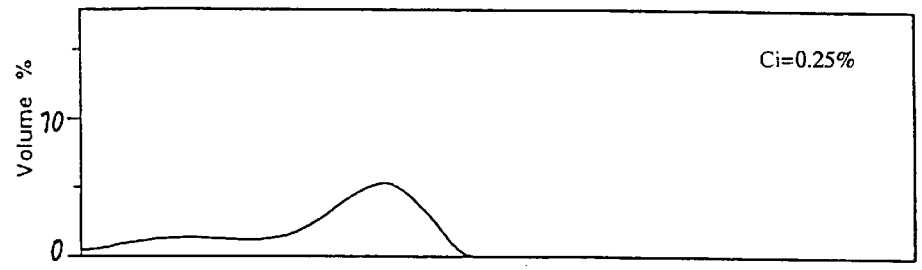
Figure 6C:
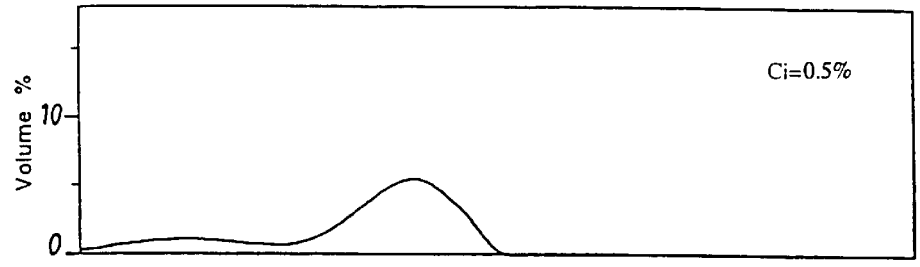
Figure 6D:
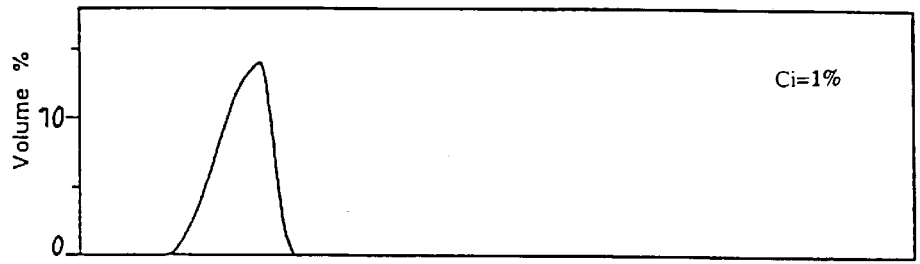
Figure 6E:
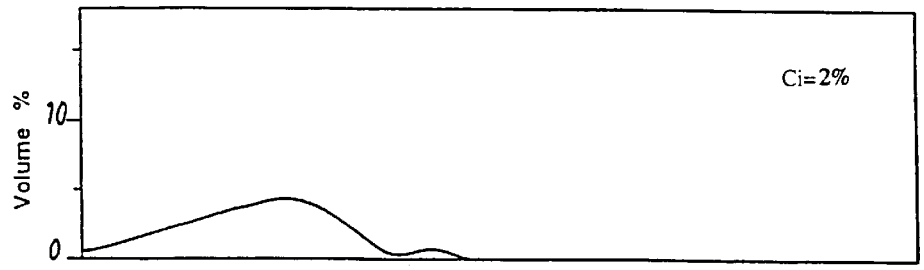
Figure 6F:
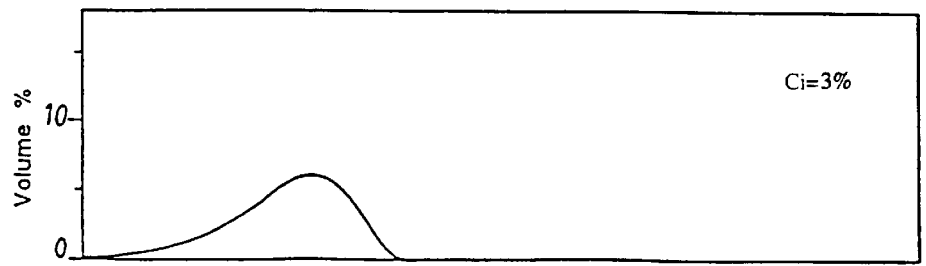

The adsorption isotherm is given in FIG. 5. Tests with this previously neutralised dicarboxylated polymer directly in butyl acetate by dimethylethanolamine have shown that the neutralised polymer adsorbs in a slightly greater amount compared to the polymer in the form of an acid.

FIGS. 6a to 6f present diagrams of granulometric analyses obtained with the aid of the COULTER LS130 apparatus for different concentrations Ci and show clearly the dispersing effect obtained with the functionalised polymer studied in this Example.

However, this polymer has no stabilising effect. In fact, a suspension of $TiO_2$ treated by this functionalised polymer sediments in less than 24 hours for levels of polymer corresponding to the plateau of the isotherm, in leaving a perfectly limpid supernatant.

Figure 7:
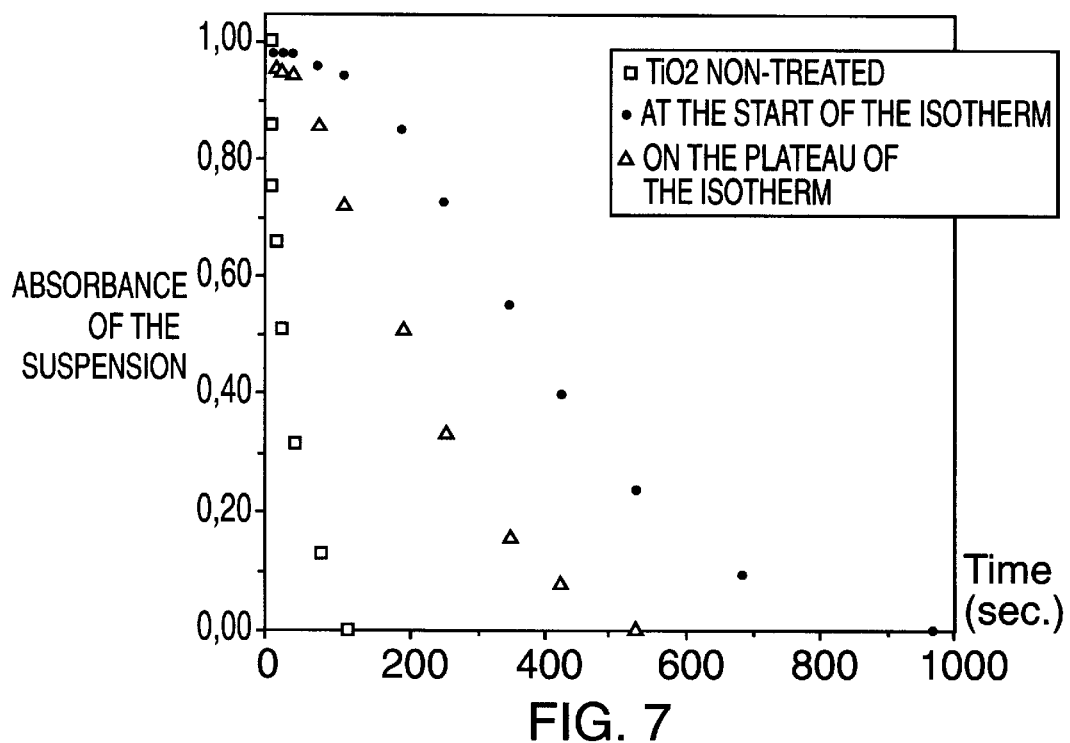

Furthermore, the curves obtained on the Shimadzu SA-CP3 <<uncross>> with the amount of polymer employed and the suspension is centrifuged much more rapidly than in the case of a stabilising polymer. These results appear clearly in FIG. 7 which gives the absorbance of a suspension of $TiO_2$ in butyl acetate in the absence of functionalised polymer (non-treated $TiO_2$), for a concentration Ci=0.5% (start of the isotherm plateau) as well as for a concentration Ci =3% (on the isotherm plateau).

Example III.1 and III.2 demonstrate that a polymer functionalised with a polar —SCH(COOH)(CH$_2$COOH) group behave like a simple dispersant or like a dispersant and a stabilising agent following the length of the polymer chain. In the case of the treatment of the TiO, in butyl acetate medium, it has been shown by us that they also become stabilising as from a minimal chain length. This is between Mn=5,000 and Mn=8,000.

III.3 - Dispersion of a titanium oxide powder.

The same powder as in Examples III.1 and III.2 is used but the functionalised polymer is poly(methyl methacrylate) functionalised at the end of the chain with a cysteine group obtained according to Example I.3.a.

Figure 8:
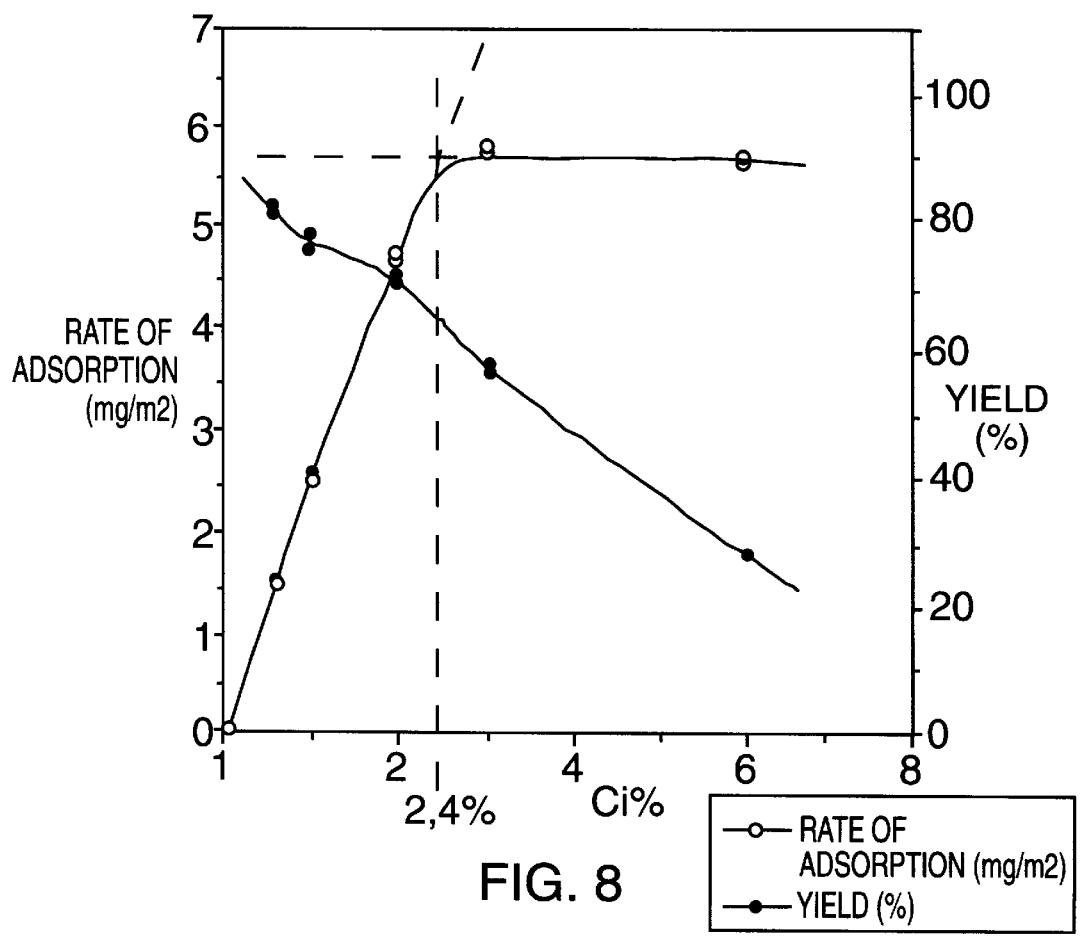
FIG. 8 is given with reference to Example III.3 and presents the adsorption isotherm of the product synthesised in Example I.3.a on a $TiO_2$ powder in a butyl acetate medium.

As in Examples III.1 and III.2, the adsorption isotherm is drawn for the $TiO_2$/functionalised polymer system in butyl acetate medium. This curve is represented in FIG. 8 enclosed which shows that the start of the plateau is reached for a value of Ci=2.4%, which corresponds to 80 mg of functionalised polymer.

III.4 - Dispersion of a titanium oxide powder.

The functionalised polymer obtained in Example I.3.b is used in this example.

Figure 9:
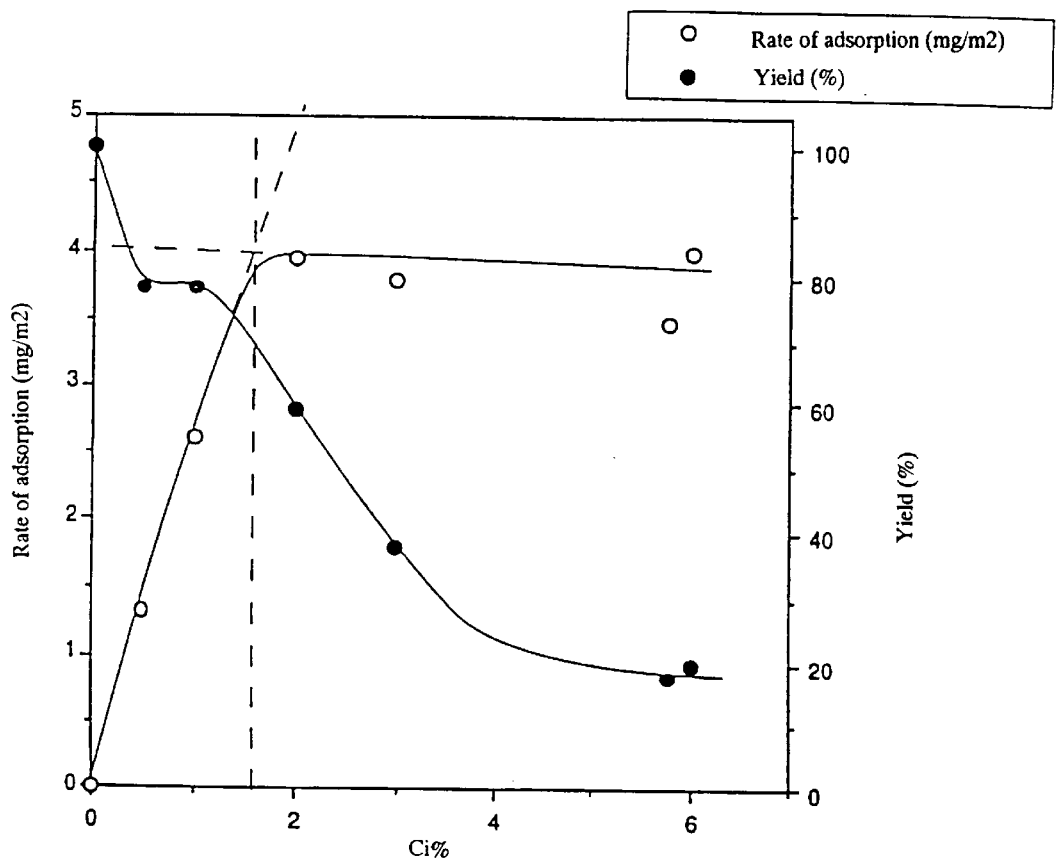
FIG. 9 is given with reference to Example III.4 and presents the adsorption isotherm of the product obtained in Example I.3.b on a $TiO_2$ powder in a butyl acetate medium.

The curves giving the rate and the yield of adsorption in terms of time are drawn as in the preceding Examples (FIG. 9).

Furthermore, the variations of the adsorption in terms of time for the non-treated $TiO_2$ suspensions are measured, as well as for the $TiO_2$ suspensions in the presence of functionalised copolymer for values of Ci of 0.5% (before the isotherm plateau) and 3% (on the isotherm plateau).

The curves giving the absorbance are represented in FIG. 10 from which it arises that the polymer disperses and stabilises $TiO_2$ in butyl acetate.

III.5 - Dispersion of a titanium oxide powder.

The functionalised polymer obtained in Example 1.4 is used in this Example.

The line of the adsorption isotherm represented in FIG. 11 shows that the start of the plateau of the isotherm corresponds to a concentration Ci of 2.6%, which signifies that it 87 mg of functionalised polymer are needed to disperse and stabilise 1 g of $TiO_2$.

Measurements of dispersability with the COULTER 130 and measurements of the absorption of the suspension confirm the dispersing effect and the stabilising effect of the product.

III.6 - Dispersion of an alumina pigment covered with an organic colorant.

The dispersion medium used is butyl acetate.

The powder to be dispersed is constituted of an alumina pigment covered with an organic colorant: C 694424 yellow pigment from MAPRECOS.

The functionalised polymer is poly(methyl methacrylate) functionalised at the end of the chain, obtained according to Example I.1.d..

FIG. 12 , which gives by evaluation with the aid of the COULTER S130 apparatus, the size of the particles obtained in the absence of functionalised polymer (non-treated) and for a concentration Ci=3%, demonstrates the dispersing effect of the product.

FIG. 13 which gives the absorbance of a suspension of yellow pigment in butyl acetate in the presence of functionalised polymer (non-treated pigment) and in the presence of functionalised polymer for a concentration Ci=3% clearly showing the stabilising effect of this polymer on the dispersion.

III.7 - Dispersion of an organic pigment

The pigment studied is a red pigment, C19025 from MAPRECOS.

The functionalised polymer is that studied in Example III.6

As in Example I1.6, the effect of a concentration Ci 3% of functionalised polymer is studied on the dispersability of the powder by measurement with the COULTER LS130 and the stability of the dispersion by measuring the absorbance and, as in the preceding Examples, the dispersant and stabilising character of the studied functionalised polymer dispersion is demonstrated.

IV -Demonstration of the surfactant effect: Formation of micelles, preparation of microlatexes and of microgels.

IV.1 - With the product of Example I.1.a 5 g of polymer obtained according to Example I.1.a are dissolved in 250 ml of THF.

The number of moles of —COOH functions to be neutralised is determined by an acido-basic determination,: here 7.87 10$^{-3}$ mol and an excess of base is added i.e. 8.2 10$^{-3}$mol.

0.73 g of DMEA (dimethylethanolamine) are dissolved in 500 g of water.

The organic polymer solution is added slowly with stirring to the aqueous solution of the amine.

The mixture obtained is distilled under reduced pressure so as to remove the THF, then it is filtered.

A micellar solution presenting a Tyndall effect is thus obtained.

The size of the micelles measured on the COULTER N4 (light diffusion) is about 4.6±1.4 nm.

This type of micelle can be used in the preparation of microlatex.

An example of formulation of such a latex is given below:
150 g of water
0.9 g of surfactant (neutralised functionalised polymer)
2.7 g of MMA
0.3 of BDMA (1,4-butanediol dimethacrylate)
0.075 g of potassium persulphate.
0.046 g of $NaHCO_3$ as buffer.

The polymerisation is carried out in a double cased reactor equipped with a stirring anchor, a condenser and a nitrogen inlet.

The micellar solution is introduced into the reactor in which it is heated at 65° C. and deoxygenated for one hour by bubbling in nitrogen. To this stirred solution at 250 tr/min. is added the mixture of monomers. The initiator is introduced in the form of an aqueous solution after 15 to 20 minutes of emulsification.

The polymerisation is then left to proceed under an atmosphere of nitrogen for about 20 hours.

In the case of the preceding formulation, the size of the microlatex obtained is measured on the COULTER N4; the results are the following:

average diameter by weight: Dw=28.6±1.4 nm average diameter by number: Dn=23.7±3.2 nm The microlatex thus prepared by using the functionalised polymer as surfactant provides different advantages summed up below:

The hydrophobic chain is of the same nature as the core of the particle. There is therefore a contribution of material in addition to the surfactant role.

This microlatex is cross-linked. It can therefore be transferred in a solvent medium in order to give a microgel.

The microlatex cited above has been dried and then redispersed in butyl acetate.

The size of the microgel obtained is measured on the COULTER N4:

Dw=36.9±0.8 nm.

The inflation of the particles in butyl acetate compared to water is noticed.

IV.2 - With the product of Example 1.2

2.5 g of polymer obtained according to Example 1.2 are dissolved in 250 ml of THF.

According to the acido-basic determination in THF medium of the polymer by potassium hydroxide, there are 2.98 $10^{-3}$ moles of —COOH to be neutralised. Neutralisation is carried out by an excess of base, here 3.37 $10^{-3}$ moles, making 0.3 g of DMEA.

These 0.3 g of DMEA are dissolved in 250 ml of water.

The organic polymer solution is added slowly, with stirring, to the aqueous solution of the amine. The mixture obtained is distilled under reduced pressure so as to remove the THF, and then filtered.

The size of the micelles measured on the COULTER N4 is about 5.5±0.6 nm.

This type of micelles may be engaged in the preparation of microlatex.

A microlatex is prepared as in the preceding Example under the same conditions of synthesis.

The size of the microlatex thus obtained is measured on the COULTER N4:

Dw=27.4±1.6 nm

Dn=22.5±2.5 nm.

The same advantages as in the preceding Example are obtained with this functionalised polymer:

contribution of material as in the preceding Example

The hydrophobic chain of the polymer comprises pendant allylic groups which are capable of copolymerising with the particle core.

The surfactant is thus chemically linked to the particle.

The cross-linked microlatex cited above was dried and then redispersed in butyl acetate.

The size of the microgel obtained is measured on the COULTER N4:

Dw=38.8±2.0 nm

IV.3 - With the product of Example I.3.c 2.5 g of polymer are dissolved in 250 ml of THF.

The number of moles of —COOH functions to be neutralised is determined by an acido-basic determination: here: $7.4.10^{-4}$ moles and an excess of base is added, making about $8.5.10^{-4}$ moles.

$8.5.10^{-4}$ moles of potassium hydroxide (KOH) are dissolved in 250 ml of water.

the organic polymer solution is added slowly, with stirring, to the aqueous potassium hydroxide solution.

The mixture obtained is distilled under reduced pressure so as to remove the THF, and then filtered on Goosh of porosity No. 4.

The resulting solution can be engaged in the preparation of microlatex.

An example of formulation of such a latex is given below:
150 g of water
0.35 g of surfactant (neutralised functionalised polymer)
2.7 g of MMA
0.3 g of BDMA
2×0.075 g of AIBN
0.046 g of $NaHCO_3$ the polymerisation is carried out in a double cased reactor, equipped with a stirring anchor, a condenser and a nitrogen inlet.

The emulsion constituted of water, surfactant, monomers and $NaHCO_3$ is prepared with vigorous stirring and is deoxygenated by bubbling in nitrogen.

0.075 g of AIBN dissolved in 2 g of a ketone are introduced after 15 to 20 minutes.

After 4 hours, 0.075 g of AIBN in 2 g of acetone are re-introduced into the reactor.

The polymerisation is then left to proceed under an atmosphere of nitrogen for a period of time of about 20 hours.

In the case of the preceding formulation, the size of the microlatex obtained is measured on the COULTER N4. The results are the following:
average diameter by weight: Dw=63.0±1.7 nm
average diameter by number: Dn=59.7±2.5 nm The microlatex thus prepared in using the functionalised polymer as surfactant has different advantages summarised below:

The hydrophobic chain is of the same nature as the core of the particle. There is therefore a contribution of material in addition to the surfactant role.

This microgel is cross-linked. It may therefore be transferred in a solvent medium in order to give a microgel.

V - Applications in cosmetics field: compositions according to the invention intended for the preparation of nail varnishes In the Examples below, the percentages are given by weight, unless otherwise stated.

According to a prior art method well-known to the person skilled in the art, nail varnishes are prepared from <<colouring solutions>> of different tints, which are mixed with a base for nail varnishes.

These <<colouring solutions>> are in fact dispersions of pigments in a base containing nitrocellulose, it being possible for this base to be the same as that used for the final formulation of the varnish. Preferably, the pigments are ground beforehand in a solvent, such as butyl acetate, by means of an appropriate grinder such as for example a ball grinder of the Dyno-mill type.

Following the present invention, the grinding of the pigment is carried out in the presence of the functionalised polymer according to the invention, used as agent which facilitates the dispersion of the pigment in the solvent.

Preferably, the proportion of polymer used is in the order of 2 to 7% with respect to the weight of the pigment. More preferably still, this proportion is about 5%.

Thus, the following grindings have been prepared:
grinding n°1 :
Black iron oxide $Fe_3O_4$ 50%
Functionalised polymer according to Example I.1.b 2.5%
Butyl acetate qs for 100%
grinding n°2:
Titanium oxide $TiO_2$ 70%
Functionalised polymer according to Example I.1.d 2.8%
Butyl acetate qs for 100%
grinding n°3
Red Organic Pigment DC Red 7 25%
Functionalised polymer according to Example I.1.c 1.25%
Butyl acetate qs for 100%

As it has been shown above, the grindings are incorporated into a <<diluting>> nitrocellulose base for preparing various colouring solutions, each one having its own tint according to the nature and the concentration of the pigment that it contains.

For example, the composition of the <<diluting>> base is the following:

| nitrocellulose | 10 to 30%, | for example 15% |
| --- | --- | --- |
| Lustralite ® (arylsulfonamide) | 8 to 15%, | for example 10% |
| dibutyl-phthalate | 4 to 7%, | for example 5% |
| Neocryl ® (acrylic resin) | 0 to 5%, | for example 2% |
| butyl acetate | 5 to 50%, | for example 20% |
| ethyl acetate | 5 to 50%, | for example 20% |
| bentonite | 0.8 to 1.5%, | for example 1% |
| toluene | 0 to 30%, | for example 25% |
| isopropanol | 1 to 5%, | for example 2% |
| | 100% | 100% | the amount of grinding introduced into the diluting base is such that the concentration of pigment in the colouring solution is generally lower than or equal to about 20%.

Following the desired tint of the final nail varnish composition, different colouring solutions at different concentrations are introduced into a base, such as the base above. The pigment content of the final nail varnish is generally in the order of 2 to 4%.

We claim:

1. Functionalised polymer of formula:

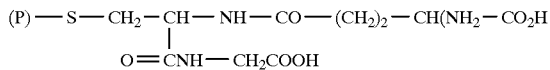

in which the COOH and/or $NH_2$ functions are free or salified and wherein (P) is a hydrophobic polymer chain obtained by radical polymerisation of at least one monomer leading to the polymer chain (P) in the presence of a chain transfer agent constituted of glutathione.

2. Functionalised polymer of the formula:

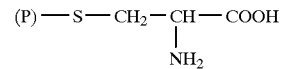

in which the COOH and/or $NH_2$ functions are free or salified and (P) is a hydrophobic polymer obtained by radical polymerisation of at least one monomer in the presence of cysteine or homocysteine acting as chain transfer agent.

3. Funtionalised polymer of the formula:

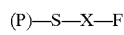

in which
(P) is a hydrophobic polymer chain obtained by radical polymerisation of at least one monomer,
S is sulphur,
X is a peptide constituted of 2 to 4 amino acids, obtained by radical polymerisation of at least one monomer leading to the formation of said polymer chain (P) in the presence of a peptide bearing at least one disulfide group and/or at least one thiol function.

4. A method for dispersing solid particles in a liquid medium comprising the step of combining with said solid particles a functionalised polymer of the formula:

in which:
(P) is a hydrophobic polymer chain of number average molar weight between 500 and 250,000, obtained by radical polymerisation of at least one monomer,
S represents sulphur,
X is selected from the group consisting of:
a saturated or unsaturated linear or branched hydrocarbon chain having 1 to 6 carbon atoms and substituted with at least one COOH or $NH_2$ group, in the free or salified form; and
a peptide chain constituted of 2 to 4 amino acids,
F represents a COOH or $NH_2$ group, in the free or salified form, or a hydrophobic polymer resulting from the radical polymerisation of at least one monomer in the presence of a peptide bearing at least one disulphide group and/or at least one thiol function.

5. The method of claim 4 wherein said liquid medium is an organic medium.

6. The method of claim 4 wherein said functionalised polymer has a number average molecular mass greater than 1,000, and said liquid medium is an organic medium.

7. The method of claim 4 wherein said particles are selected from the group consisting of metallic oxide particles, metallic oxide covered with organic colorant molecules, and organic particles, coprecititated with an organic colorant.

8. The method of claim 4 wherein said functionalised polymer has a number molar mass lower than 20,000 and is used for preparation of a micellar solution or a microdispersion of polymers.

9. The method of claim 4 wherein said functionalised polymer results from the radical polymerisation of a monomer leading to a hydrophobic polymer chain in the presence of a thiol of formula H—S—X—F or a disulphide of formula F—X—S—S—X—F, said thiol or disulphide acting as a chain transfer agent during said radical polymerisation, said monomer(s) leading to the formation of the polymer chain (P).

10. The method of claim 4 wherein said F—X part comprises at least one carboxylic function and at least one amine function, in the free or salified form.

11. The method of claim 4 wherein said functionalised polymer is of the formula:

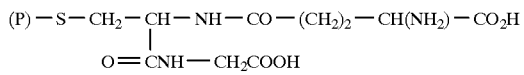

12. The method of claim 4 wherein said functionalised polymer is obtained by radical polymerisation of a monomer leading to the polymerised chain in the presence of a chain transfer agent constituted of glutathione.

13. The method of claim 4 wherein said functionalised polymer is obtained by radical polymerisation of at least one monomer leading to a hydrophobic polymer chain, in the presence of cysteine or homocysteine acting as a chain transfer agent.

14. The method of claim 4 wherein said functionalised polymer is obtained by radical polymerisation of at least one monomer leading to a hydrophobic polymer chain, in the presence of a peptide bearing at least one disulphide group and/or at least one thiol function.

15. The method of claim 4 wherein said monomer is an acrylic monomer selected from the group made up of the acrylates, methacrylates, ethylacrylates of a saturated or unsaturated C1 to C18 hydrocarbon group a linear, branched, or cycle-containing allylic group.

16. The method of claim 4 wherein said polymer chain is methyl polymethacrylate (PMMA).

17. A method for incorporating solid particles in a composition selected from the group consisting of paint, food, phytosanitary compositions and cosmetic compositions comprising the steps of combining said solid particles with a functionalised polymer of formula:

in which:
(P) is a hydrophobic polymer chain of number average molar weight between 500 and 250,000, obtained by radical polymerisation of at least one acrylic monomer,
S represents sulphur,
X is selected from the group consisting of:
a saturated or unsaturated linear or branched hydrocarbon chain having 1 to 6 carbon atoms and substituted with at least one COOH or $NH_2$ group, in the free or salified form; and
a peptide chain constituted of 2 to 4 amino acids,
F represents a COOH or $NH_2$ group, in the free or salified form, or a polymer resulting from the radical polymerisation of at least one monomer leading to a hydrophobic polymer chain in the presence of a peptide bearing at least one disulphide group and/or at least one thiol function;
and adding said combined solid particles and functionalised polymer to said composition.

18. The method of claim 17 wherein said solid particles are pigments.

19. The method of claim 17 wherein said functionalised polymer is present in an amount of between 2% and 7% by weight compared to the total weight of the solid particles in the composition.

20. The method of claim 17 wherein said functionalised polymer is comprised in a microdispersion of polymers.

21. The method of claim 20 wherein said microdispersion of polymers is present in an amount of between 1% and 20% by weight with respect to the total weight of the composition.

22. The method of claim 17 wherein the composition is a nail varnish.

23. A cosmetic composition for the care or the make-up of nails, comprising a functionalised polymer of the formula:

in which:
(P) is a hydrophobic polymer chain of number average molar weight between 500 and 250,000,
S represents sulphur,
X is selected from the group consisting of:
a saturated or unsaturated linear or branched hydrocarbon chain having 1 to 6 carbon atoms and substituted with at least one COOH or $NH_2$ group, in the free or salified form, and
a peptide chain constituted of 2 to 4 natural amino acids,
F represents a COOH or $NH_2$ group, in the free or salified form, or a polymer resulting from a radical polymerisation of at least one monomer in the presence of a peptide bearing at least one disulphide group and/or at least one thiol function.

24. The cosmetic composition according to claim 23, wherein the functionalised polymer is comprised in a microdispersion of polymers.

25. The cosmetic composition of claim 23 wherein said composition further contains nitrocellulose.

26. A surfactant having the formula:

in which:
(P) is a hydrophobic polymer chain of number average molar weight between 500 and 250,000, obtained by radical polymerisation of at least one monomer,
S represents sulphur,
X is selected from the group consisting of:
a saturated or unsaturated linear or branched hydrocarbon chain having 1 to 6 carbon atoms and substituted with at least one COOH or $NH_2$ group, in the free or salified form; and
a peptide chain constituted of 2 to 4 amino acids,
F represents a COOH or $NH_2$ group, in the free or salified form, or a hydrophobic polymer resulting from the radical polymerisation of at least one monomer in the presence of a peptide bearing at least one disulphide group and/or at least one thiol function.

27. A method to improve the wetting effect of a liquid medium towards a solid surface or particle comprising the step of adding to said liquid medium an effective amount of a functionalised polymer of the formula:

in which:
(P) is a hydrophobic polymer chain of number average molar weight between 500 and 250,000, obtained by radical polymerisation of at least one monomer, S represents sulphur, X is selected from the group consisting of:
  a saturated or unsaturated linear or branched hydrocarbon chain having 1 to 6 carbon atoms and substituted with at least one COOH or NH$_2$ group, in the free or salified form; and
  a peptide chain constituted of 2 to 4 amino acids, F represents a COOH or NH$_2$ group, in the free or salified form, or a hydrophobic polymer resulting from the radical polymerisation of at least one monomer in the presence of a peptide bearing at least one disulphide group and/or at least one thiol function.

28. A method for forming an emulsion comprising the step of combining two liquids with a surfactant to form a liquid-liquid emulsion, said surfactant being a functionalised polymer of the formula:

$$(P)\text{—}S\text{—}X\text{—}F \quad (1')$$

in which:
  (P) is a hydrophobic polymer chain of number average molar weight between 500 and 250,000, obtained by radical polymerisation of at least one monomer,
  S represents sulphur,
  X is selected from the group consisting of:
    a saturated or unsaturated linear or branched hydrocarbon chain having 1 to 6 carbon atoms and substituted with at least one COOH or NH$_2$ group, in the free or salified form, and
    a peptide chain constituted of 2 to 4 amino acids;
  F represents a COOH or NH$_2$ group, in the free or salified form, or a hydrophobic polymer resulting from the radical polymerisation of at least one monomer in the presence of a peptide bearing at least one disulphide group and/or at least one thiol function.

29. The method of claim 28 wherein said functionalised polymer results from the radical polymerisation of a monomer leading to a hydrophobic polymer chain in the presence of a thiol of formula H—S—X—F or a disulphide of formula F—X—S—S—X—F, said thiol or disulphide acting as a chain transfer agent during said radical polymerisation, said monomer(s) leading to the formation of the polymer chain (P).

30. The method of claim 28 wherein said F—X part comprises at least one carboxylic function and at least one amine function, in the free or salified form.

31. The method of claim 28 wherein said functionalised polymer is of the formula:

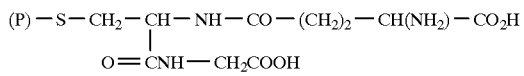

(P)—S—CH$_2$—CH—NH—CO—(CH$_2$)$_2$—CH(NH$_2$)—CO$_2$H
              |
         O=CNH—CH$_2$COOH

32. The method of claim 31 wherein said functionalised polymer is obtained by radical polymerisation of a monomer leading to the polymerised chain in the presence of a chain transfer agent constituted of glutathione.

33. The method of claim 28 wherein said functionalised polymer is obtained by radical polymerisation of at least one monomer leading to a hydrophobic polymer chain, in the presence of cysteine or homocysteine acting as a chain transfer agent.

34. The method of claim 28 wherein said functionalised polymer is obtained by radical polymerisation of at least one monomer leading to a hydrophobic polymer chain, in the presence of a peptide bearing at least one disulphide group and/or at least one thiol function.

35. The method of claim 28 wherein said monomer is an acrylic monomer selected from the group made up of the acrylates, methacrylates, ethylacrylates of a saturated or unsaturated linear, branched, or cycle-containing C1 to C18 hydrocarbon group.

36. The method of claim 28 wherein said polymer chain is methyl polymethacrylate (PMMA).

37. A method for incorporating solid particles in cosmetic compositions comprising the steps of combining said solid particles with a functionalised polymer of formula:

$$(P)\text{—}S\text{—}X\text{—}F \quad (1')$$

in which:
  (P) is a hydrophobic polymer chain of number average molar weight between 500 and 250,000, obtained by radical polymerisation of at least one acrylic monomer,
  S represents sulphur,
  X is selected from the group consisting of:
    a saturated or unsaturated linear or branched hydrocarbon chain having 1 to 6 carbon atoms and substituted with at least one COOH or NH$_2$ group, in the free or salified form, and
    a peptide chain constituted of 2 to 4 amino acids,
  F represents a COOH or NH$_2$ group, in the free or salified form, or a polymer resulting from the radical polymerisation of at least one monomer leading to a hydrophobic polymer chain in the presence of a peptide bearing at least one disulphide group and/or at least one thiol function;
  and adding said combined solid particles and functionalised polymer to said composition.

38. The method of claim 37 wherein said solid particles are pigments.

39. The method of claim 37 wherein said functionalised polymer is present in an amount of between 2% and 7% by weight compared to the total weight of the solid particles in the composition.

40. The method of claim 37 wherein said functionalised polymer is comprised in a microdispersion of polymers.

41. The method of claim 40 wherein said microdispersion of polymers is present in an amount of between 1% and 20% by weight with respect to the total weight of the composition.

42. The functionalised polymer of claim 7 wherein the peptide is a keratin hydrolysate.

* * * * *